(12) United States Patent
Ogasawara et al.

(10) Patent No.: US 9,248,053 B2
(45) Date of Patent: Feb. 2, 2016

(54) MANUFACTURING METHOD AND MANUFACTURING EQUIPMENT OF COMPOSITE BODY OF SHEET-LIKE MEMBER OF ABSORBENT ARTICLE

(75) Inventors: Yoshikazu Ogasawara, Kagawa (JP); Noriaki Ito, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 997 days.

(21) Appl. No.: 13/133,771

(22) PCT Filed: Dec. 10, 2009

(86) PCT No.: PCT/JP2009/070659
§ 371 (c)(1),
(2), (4) Date: Aug. 11, 2011

(87) PCT Pub. No.: WO2010/071069
PCT Pub. Date: Jun. 24, 2010

(65) Prior Publication Data
US 2011/0287918 A1    Nov. 24, 2011

(30) Foreign Application Priority Data

Dec. 18, 2008    (JP) ................................. 2008-322777

(51) Int. Cl.
*A61F 13/15*    (2006.01)
*A61F 13/496*    (2006.01)

(52) U.S. Cl.
CPC ............ *A61F 13/15699* (2013.01); *A61F 13/15* (2013.01); *A61F 13/15764* (2013.01); *A61F 13/496* (2013.01); *A61F 13/15593* (2013.01)

(58) Field of Classification Search
USPC .................................. 493/393–394, 379–380
IPC .... B32B 37/00,37/10, 37/1009, 37/1018; A61F 13/15, 13/15593, 13/15764, 13/15669
See application file for complete search history.

(56) References Cited

U.S. PATENT DOCUMENTS

| 4,726,876 A |   | 2/1988 | Tomsovic, Jr. |
| 5,091,039 A | * | 2/1992 | Ujimoto et al. ............... 156/519 |

(Continued)

FOREIGN PATENT DOCUMENTS

| EP | 1162162 A1 | 12/2001 |
| EP | 1415628 A1 | 5/2004 |

(Continued)

OTHER PUBLICATIONS

Office Action mailed Nov. 26, 2013 corresponds to Japanese patent application No. 2008-322777.

(Continued)

*Primary Examiner* — Christopher Harmon
(74) *Attorney, Agent, or Firm* — Hauptman Ham, LLP

(57) ABSTRACT

A method of manufacturing a composite body of a sheet-like member of an absorbent article, the method includes: holding a first sheet-like member on a holding surface of a holding section; and delivering and attaching the first sheet-like member from the holding surface to a second sheet-like member. The first sheet-like member has a section that is to be delivered first, and a section that is to be delivered subsequently during delivery to the second sheet-like member. The first sheet-like member is held on the holding surface with suction air from a plurality of holes that have been formed on the holding surface. The holding section has at least two suction chambers. A first suction chamber is in communication with holes that suck the section that is to be delivered first, and a second suction chamber is in communication with holes that suck the section that is to be delivered subsequently.

16 Claims, 18 Drawing Sheets

(56) References Cited

U.S. PATENT DOCUMENTS

| | | | |
|---|---|---|---|
| 6,719,031 B2 * | 4/2004 | Sawai | 156/519 |
| 6,722,494 B2 * | 4/2004 | Nakakado | 198/792 |
| 7,341,087 B2 * | 3/2008 | Tabor et al. | 156/538 |
| 7,533,709 B2 * | 5/2009 | Meyer | 156/517 |
| 8,607,959 B2 * | 12/2013 | Papsdorf et al. | 198/377.04 |
| 8,673,098 B2 * | 3/2014 | McCabe | 156/163 |
| 8,820,513 B2 * | 9/2014 | Papsdorf et al. | 198/478.1 |
| 2002/0125105 A1 | 9/2002 | Nakakado | |
| 2004/0089403 A1 | 5/2004 | Satoh | |
| 2007/0074953 A1 * | 4/2007 | McCabe | 198/377.08 |
| 2008/0196564 A1 * | 8/2008 | McCabe | 83/23 |
| 2010/0012458 A1 * | 1/2010 | Giuliani et al. | 198/377.04 |

FOREIGN PATENT DOCUMENTS

| | | | |
|---|---|---|---|
| EP | 2301875 A1 | 3/2011 | |
| JP | 62191314 A | 8/1987 | |
| JP | 1-143752 A | 10/1989 | |
| JP | 04-032437 A | 2/1992 | |
| JP | 2002-193440 A | 7/2002 | |
| JP | 2004-148040 A | 5/2004 | |
| JP | 2005-145597 A | 6/2005 | |
| JP | 2005-298193 A | 10/2005 | |
| WO | 01/44086 A1 | 6/2001 | |

OTHER PUBLICATIONS

Office Action issued by the Chinese Patent Office on Dec. 31, 2012 in corresponding Chinese Application No. 200980100899.1.
International Search Report for PCT/JP2009/070659 mailed Mar. 16, 2010.
Supplementary European Search Report issued Apr. 19, 2013 corresponds to EP Patent application No. 09833372.7.
Office Action issued Apr. 28, 2014, corresponds to European patent application No. 09833372.7.

* cited by examiner

LONGITUDINAL DIRECTION

B-B ARROW VIEW

C-C ARROW VIEW

B-B ARROW VIEW

C-C ARROW VIEW

B-B ARROW VIEW

C-C ARROW VIEW

MANUFACTURING METHOD AND MANUFACTURING EQUIPMENT OF COMPOSITE BODY OF SHEET-LIKE MEMBER OF ABSORBENT ARTICLE

RELATED APPLICATION

The present application is a National Phase of International Application Number PCT/JP2009/070659, filed Dec. 10, 2009, and claims priority from, Japanese Application Number 2008-322777, filed Dec. 18,2008.

TECHNICAL FIELD

The present invention relates to a manufacturing method and a manufacturing equipment of a composite body of a sheet-like member of an absorbent article.

BACKGROUND ART

In the past, in a manufacturing line of an absorbent article such as a disposable diaper and a sanitary napkin, a composite body of a sheet-like member has been manufactured by a first sheet-like member held on a holding surface of a holding section being delivered from the holding surface and attached to a second sheet-like member.

Here, holding of the first sheet-like member with this holding surface is generally performed using suction force that is generated on the holding surface with suction air from the multiple suction holes that have been formed on the holding surface. Further, these suction holes are in communication with just one suction chamber that has been partitioned and formed inside the holding section, and suction is performed from the suction holes based on a negative pressure state of this suction chamber (refer to PTL 1).

CITATION LIST

Patent Literature

[PTL 1] Japanese patent Application Laid-open Application No. 2005-298193

SUMMARY OF INVENTION

Technical Problem

However, during delivering, in the case that a delivering timing partially shifts, such that one part of the first sheet-like member is delivered first and the remaining part is delivered subsequently, when one part has been delivered, the suction holes that had been sucking this one part are already not covered by the first sheet-like member, so that they can suck with a small suction resistance and the negative pressure level of the suction chamber can foe decreased. As a result, there was a possibility that the suction force of the suction holes sucking the remaining part to be delivered subsequently becomes smaller, and that holding property of the remaining part decreased before delivery. Then, there was a possibility that with the decrease of this holding property the first sheet-like member was deformed or the like, and attaching precision to the second sheet-like member was decreased.

This invention has been made in view of the above problems, and an object thereof is to provide a manufacturing method and manufacturing equipment of a composite body of a sheet-like member in which attaching precision of the first sheet-like member can be increased when delivering and attaching the first sheet-like member to the second sheet-like member, in order to manufacture the composite body of the sheet-like member of an absorbent article.

Solution to Problem

An aspect of the invention to achieve the above object is a method of manufacturing a composite body of a sheet-like member of an absorbent article, the method including:
holding a first sheet-like member on a holding surface of a holding section; and delivering and attaching the first sheet-like member from the holding surface to a second sheet-like member,
the first sheet-like member having a section that is to be delivered first and a section that is to be delivered subsequently during delivery to the second sheet-like member, the first sheet-like member being held on the holding surface with suction air from a plurality of holes that have been formed on the holding surface,
the holding section having at least two suction chambers of a first suction chamber that is in communication with holes that suck the section that is to be delivered first and a second suction chamber that is in communication with holes that suck the section that is to be delivered subsequently,
the first sheet-like member being delivered to the second sheet-like member in a state in which the first suction chamber and the second suction chamber have been partitioned so as not to allow air to pass through to each other.

Further, another aspect of the invention is a manufacturing equipment of a composite body of a sheet-like member of an absorbent article, including:
a holding section including a holding surface,
the holding section holding a first sheet-like member on the holding surface and delivering and attaching the first sheet-like member from the holding surface to a second sheet-like member,
the first sheet-like member having a section to be delivered first and a section to be delivered subsequently during delivery to the second sheet-like member, the first sheet-like member being held on the holding surface with suction air from a plurality of holes that have been formed on the holding surface,
the holding section having at least two suction chambers of a first suction chamber that is in communication with holes that suck the section to be delivered first and a second suction chamber that is in communication with holes that suck the section to be delivered subsequently,
the holding section delivering the first sheet-like member to the second sheet-like member in a state in which the first suction chamber and the second suction chamber have been partitioned so as not to allow air to pass through to each other.

Other features of this invention will become apparent from the description in this specification and the attached drawings.

Advantageous Effects of Invention

According to this invention, an attaching precision when delivering and attaching the first sheet-like member to the second sheet-like member can be increased.

BRIEF DESCRIPTION OF DRAWINGS

FIG. 12 is an illustrative picture of an example of a suction air configuration.

DESCRIPTION OF EMBODIMENTS

Figure 1:
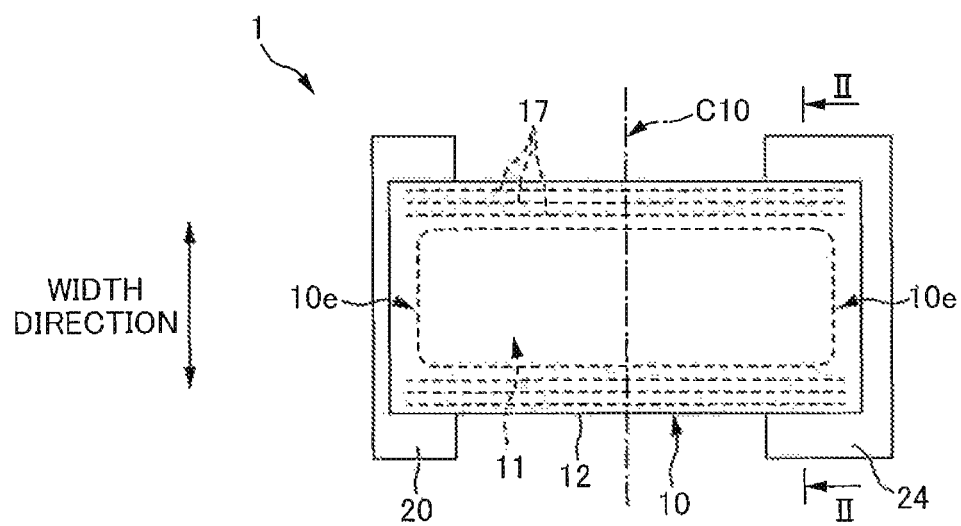
FIG. 1 is a plan view of a disposable diaper 1.

With the description of this specification and the attached diagrams, at least the below matters will become clear.

A method of manufacturing a composite body of a sheet-like member of an absorbent article, the method including:

holding a first sheet-like member on a holding surface of a holding section; and delivering and attaching the first sheet-like member from the holding surface to a second sheet-like member, the first sheet-like member having a section that is to be delivered first and a section that is to be delivered subsequently during delivery to the second sheer-like member, the first sheet-like member being held on the holding surface with suction air from a plurality of holes that have been formed on the holding surface, the holding section having at least two suction chambers of a first suction chamber that is in communication with holes that suck the section that is to be delivered first and a second suction chamber that is in communication with holes that suck the section that is to be delivered subsequently, the first sheet-like member being delivered to the second sheet-like member in a state in which the first suction chamber and the second suction chamber have been partitioned so as not to allow air to pass through to each other.

According to such a manufacturing method of a composite body of a sheet-like member of an absorbent article, the first sheet-like member is delivered to the second sheet-like member, in a state in which the first suction chamber and the second suction chamber are partitioned so as not to allow air to pass through to each other. Therefore, during delivery, a suction air state of the first suction chamber can be made to have little effect on the second suction chamber. That is to say, decrease of suction force of the holes of the section to be delivered subsequently that may occur after delivery of the section to be delivered first to the second sheer-like member can be effectively prevented, and as a result the holding surface can surely hold the first sheet-like member from the beginning to the end of the series of the delivery operations. Therefore, deformation and the like of the first sheet-like member can be effectively suppressed, and the attaching precision can be improved.

A manufacturing method of a composite body of a sheet-like member of an absorbent article, wherein preferably in response to a delivery operation of the section to be delivered first to the second sheet-like member, suction air of the holes that suck the section to be delivered first is weakened, and in response to a delivery operation of the section to be delivered subsequently to the second sheet-like member, suction air of the holes that suck the section to be delivered subsequently is weakened.

According to such a manufacturing method of a composite body of a sheet-like member of an absorbent article, the suction air of the holes are weakened, in response to a delivery operation of a section that the holes of the first sheet-like member are in charge of, thus the suction force of the holes can be weakened, and delivery of the first sheet-like member from the holding surface to the second sheet-like member can be promptly performed.

A manufacturing method of a composite body of a sheet-like member of an absorbent article, wherein preferably the holes that have been weakened of the suction air blow out air toward the first sheet-like member in an order in which the holes have been weakened.

According to such a manufacturing method of a composite body of a sheet-like member of an absorbent article, the holes corresponding to the section that should already be delivered of the first sheet-like member sequentially blow out air, so the suction force to the section that should already be delivered can be completely ceased to exist, and as a result delivery of the first sheet-like member from the holding surface to the second sheet-like member can be performed promptly.

A manufacturing method of a composite body of a sheet-like member of an absorbent article, wherein preferably the third suction chamber is partitioned in a position in between the first suction chamber and the second suction chamber in the holding section, holes in communication with the third suction chamber are formed positioned in between the holes in communication with the first suction chamber and the holes in communication with the second suction chamber, and in a state in which the first suction chamber, the second suction chamber, and the third suction chamber have been partitioned so as not to allow air to pass through to each other, the first sheet-like member is delivered to the second sheet-like member.

According to such a manufacturing method of a composite body of a sheet-like member of an absorbent article, suction operation of the holes on the holding surface can be performed in a further subdivided state, and the holding surface can surely hold the first sheet-like member from the beginning to the end of the series of the delivery operations.

A manufacturing method of a. composite body of a sheet-like member of an absorbent article, wherein preferably the holding section moves along a trajectory, the second sheet-like member is a continuous sheet that is wrapped around a roller in a delivery position in the trajectory and that travels continuously, during the holding section passing by the delivery position along a travel direction of the second sheet-like member, the first sheet-like member on the holding surface of the holding section is delivered to the second sheet-like member, and the holes that suck the section to be delivered first have been formed in an area to be a downstream side in the trajectory of the holding surface during delivery, and the holes that suck the section to be delivered subsequently are formed in an area to be an upstream side of the holding surface.

According to such a manufacturing method of a composite body of a sheet-like member of an absorbent article, when the holding section passes by the delivery position, the first sheet-like member can be promptly delivered from the holding section to the second sheet-like member.

A manufacturing method of a composite body of a sheet-like member of an absorbent article, wherein preferably the section to be delivered first and the section to be delivered subsequently are each fixed with an elastic member that contracts these sections toward each other in a same direction, in a state in which the first sheet-like member is sucked onto the holding surface with tine suction air from the holes, the section to be delivered first and section to be delivered subsequently are held in a state extended against a contractive force from the corresponding elastic member.

According to such a manufacturing method of a composite body of a sheet-like member of an absorbent article, the effects of this manufacturing method can be effectively achieved. That is to say, according to this manufacturing method, since decrease in the suction force of the holes of the section to be delivered subsequently, which may occur after delivery of the section to be delivered first can be effectively prevented, even after delivery of the section to be delivered first, the extended state of the section to be delivered subsequently can be effectively maintained on the holding surface. As a result, a difference in a contracting amount between the section to be delivered first and the section to be delivered subsequently in the delivery process can be suppressed, and the attaching precision to the second sheet-like member can be improved.

A manufacturing method of a composite body of a sheet-like member of an absorbent article, wherein preferably the first suction chamber and the second suction chamber are partitioned inside the holding section in a chamber form so as not to allow air to pass through to each other.

According to such a manufacturing method of a composite body of a sheet-like member of an absorbent article, the first suction chamber and the second suction chamber are partitioned inside the holding section in a chamber form that does not allow air to pass through to each other, and the holding surface can surely hold the first sheet-like member from the beginning to the end of the series of the delivery operations.

Further, a manufacturing equipment of a composite body of a sheet-like member of an absorbent article, including:

a holding section including a holding surface, the holding section holding a first sheet-like member on the holding surface and delivering and attaching the first sheet-like member from the holding surface to a second sheet-like member, the first sheet-like member having a section to be delivered first and a section to be delivered subsequently during delivery to the second sheet-like member, the first sheet-like member being held on the holding surface with suction air from a plurality of holes that have been formed on the holding surface, the holding section having at least two suction chambers of a first suction chamber that is in communication with holes that suck the section to be delivered first arid a second suction chamber that is in communication with holes that suck the section to be delivered subsequently, the holding section delivering the first sheet-like member to the second sheet-like member in a state in which the first suction chamber and the second suction chamber have been partitioned so as not to allow air to pass through to each other.

According to such manufacturing equipment of a composite body of a sheer-like member of an absorbent article, in a state in which the first suction chamber and the second suction chamber are partitioned so as not to allow air to pass through to each other, the first sheet-like member is delivered to the second sheet-like member. Therefore, during delivery, the suction air state of the first suction chamber can be made so as to have little effect on the second suction chamber. That is to say, decrease in the suction force of the holes of the section to be delivered subsequently, which may occur after delivery of the section to be delivered first to the second sheet-like member can be effectively prevented, and as a result the holding surface can surely hold the first sheet-like member from the beginning to the end of the series of the delivery operations. Therefore, such as deformation of the first sheet-like member can be effectively suppressed and the attaching precision can be improved.

===The Present Embodiment===

A manufacturing method and manufacturing equipment 31 of a composite body 1*a* of a continuous sheet of an absorbent article 1 in this embodiment is applied to, for example, a manufacturing line of a disposable diaper 1.

Figure 2A:
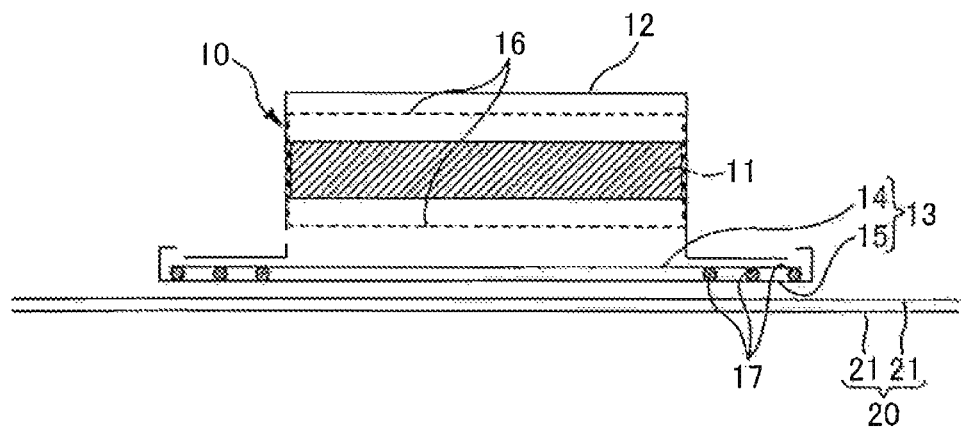
FIG. 2A is a II-II cross section view in FIG. 1.
Figure 2B:
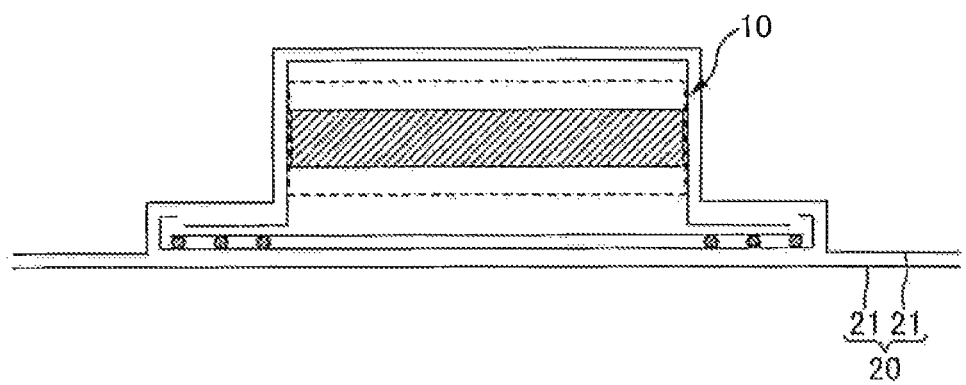
FIG. 2B is the same cross section view of another mode of the diaper 1.
Figure 3:
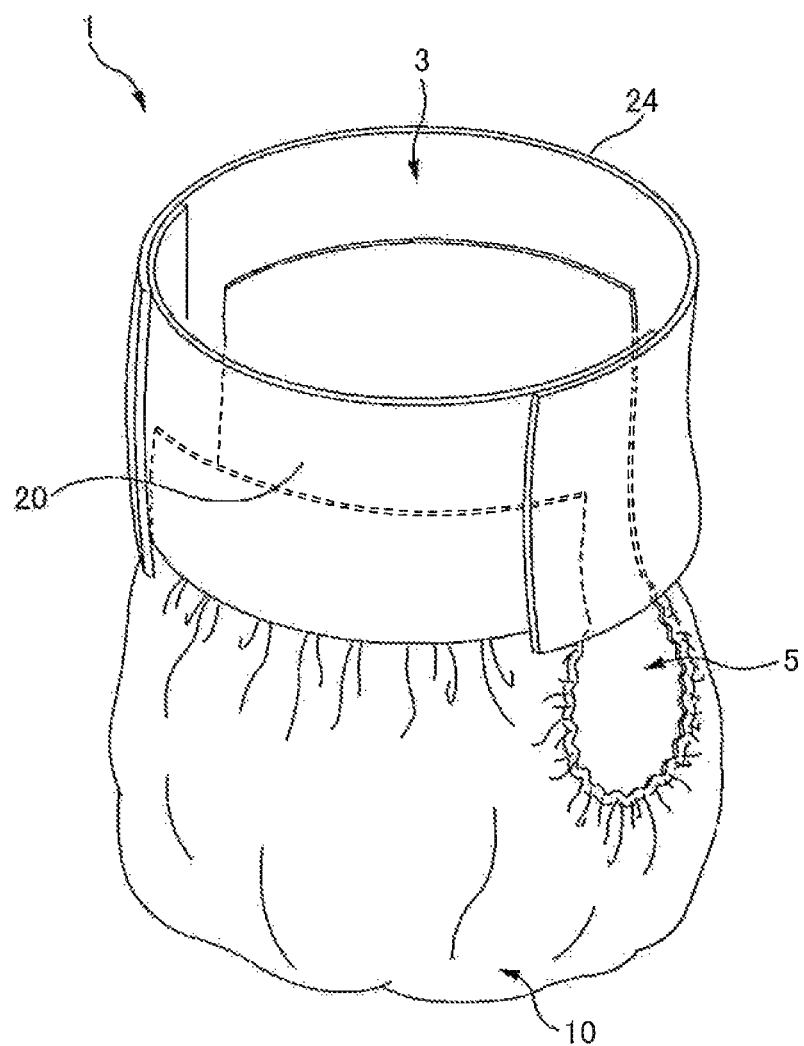
FIG. 3 is a perspective view of the diaper 1.

FIG. 1 to FIG. 3 are illustrative pictures of the disposable diaper 1. FIG. 1 is a plan view of the diaper 1, FIG. 2A is a II-II cross section view in FIG. 1, and FIG. 2B is a same cross section view of smother mode of the diaper 1. FIG. 3 is a perspective view of the diaper 1.

This diaper 1 includes an abdominal side belt member 20 that covers an abdominal side part of a wearer, a back side belt member 24 that covers a back side section, and an absorbent main body 10 that absorbs bodily fluid such as urine by being applied in between the crotches. In a developed state in FIG. 1, in a state the abdominal side belt member 20 and the back side belt member 24 are arranged in parallel with an interval therebetween, the above both end sections 10*e*, 10*e* in a longitudinal direction of the absorbent main body 10 are put across and fixed therebetween, and its exterior shape is a substantially H-shape in plan view. Then, from this state, when the diaper 1 is folded in two with a central section C10 in a longitudinal direction of the absorbent main body 10 as a folding position, and belt members 20 and 24 opposing each other in this two-fold state are fixed to sections to come in contact with sides of the wearer, these belt members 20, 24 are connected to each other in a circle, and thus become the diaper 1 in a wearing state formed with a torso opening 3 and a pair of leg openings 5, 5 such as that as shown in FIG. 3.

It should be noted that, as the above-described fixing configuration, by using a bonding configuration that cannot be removed such as welding, if becomes a pant-type diaper, and on the other hand by using a bonding configuration that can be attached and removed such as a fastening tape member (not shown), it becomes an opening-type diaper. Hereinbelow, referring to FIG. 1 and FIG. 2A, each of the configuring parts 10, 20, 24 of the diaper 1 is described.

The absorbent main body 10 includes an absorbent body 11 that is made by molding liquid absorbent fiber such as pulp fiber into a substantially rectangular shape in plan view, a surface sheet member 12 that covers the absorbent body 11 from a side to the wearer's skin, and a back surface sheet member 13 that covers the absorbent body 11 from an opposite side of the surface sheet member 12 and also serves as an exterior of the diaper 1. The absorbent body 11 may include superabsorbent polymer. The surface sheet member 12 is, for example, a fluid permeable nonwoven fabric with a size in a plane larger than the absorbent body 11. Further, the back surface sheet member 13 is a fluid non-permeable sheet with a size in a plane larger than the absorbent body 11, and as one example thereof there is given a sheet 13 having a two-layer configuration with a fluid non-permeable leakproof sheet 14 of such as polyethylene and an exterior sheet 15 such as a nonwoven fabric adhered together. Then, in a state in which the absorbent body 11 is sandwiched in between the back surface sheet member 13 arid the surface sheet member 12, in a section that lies outside of the four sides of the absorbent body 11, the back surface sheet member 13 and the surface sheet member 12 are adhered together in a frame state, and thus the absorbent main body 10 is formed.

It should be noted that, as shown in FIG. 2A, a fluid permeable sheet 16 such as a tissue paper may be interposed in between the surface sheet member 12 and the absorbent body 11 and in between the back surface sheet member 13 and the absorbent body 11. Further, in both end sections in a width direction in the back surface sheet member 13, an elastic member 17 such as an elastic string may be interposed and fixed in an extended state along a longitudinal direction in between the leakproof sheet 14 and the exterior sheet 15, and in this way with these elastic members 17 each of the leg openings 5, 5 of the diaper 1 are formed with an around-leg gather section and elasticity is given.

The abdominal side belt member 20 and the back side belt member 24 both have, for example, a flexible sheet such as a nonwoven fabric as the material. Here, as shown in FIG. 2A, each of the belt members 20, 24 are formed by double layering the nonwoven fabrics 21, 21, and each of the belt members 20, 24 are adhered to and fixed to the corresponding end sections 10e, 10e in the longitudinal direction, of the absorbent main body 10. But, as shown in FIG. 2B, the end sections 10e, 10e in the longitudinal direction of the absorbent main body 10 may be interposed and fixed in between the double layered nonwoven fabrics 21, 21. Further, each of the belt members 20, 24 may be fixed with an elastic member such as an elastic string in an extended state, and these belt members 20, 24 may be given elasticity.

Such a diaper 1 is completed, with any part that continuously flows in a manufacturing line as a base material, by such as bonding various parts to this base material. The manufacturing method and the manufacturing equipment 31 according to this embodiment serve one step thereof.

Figure 4:
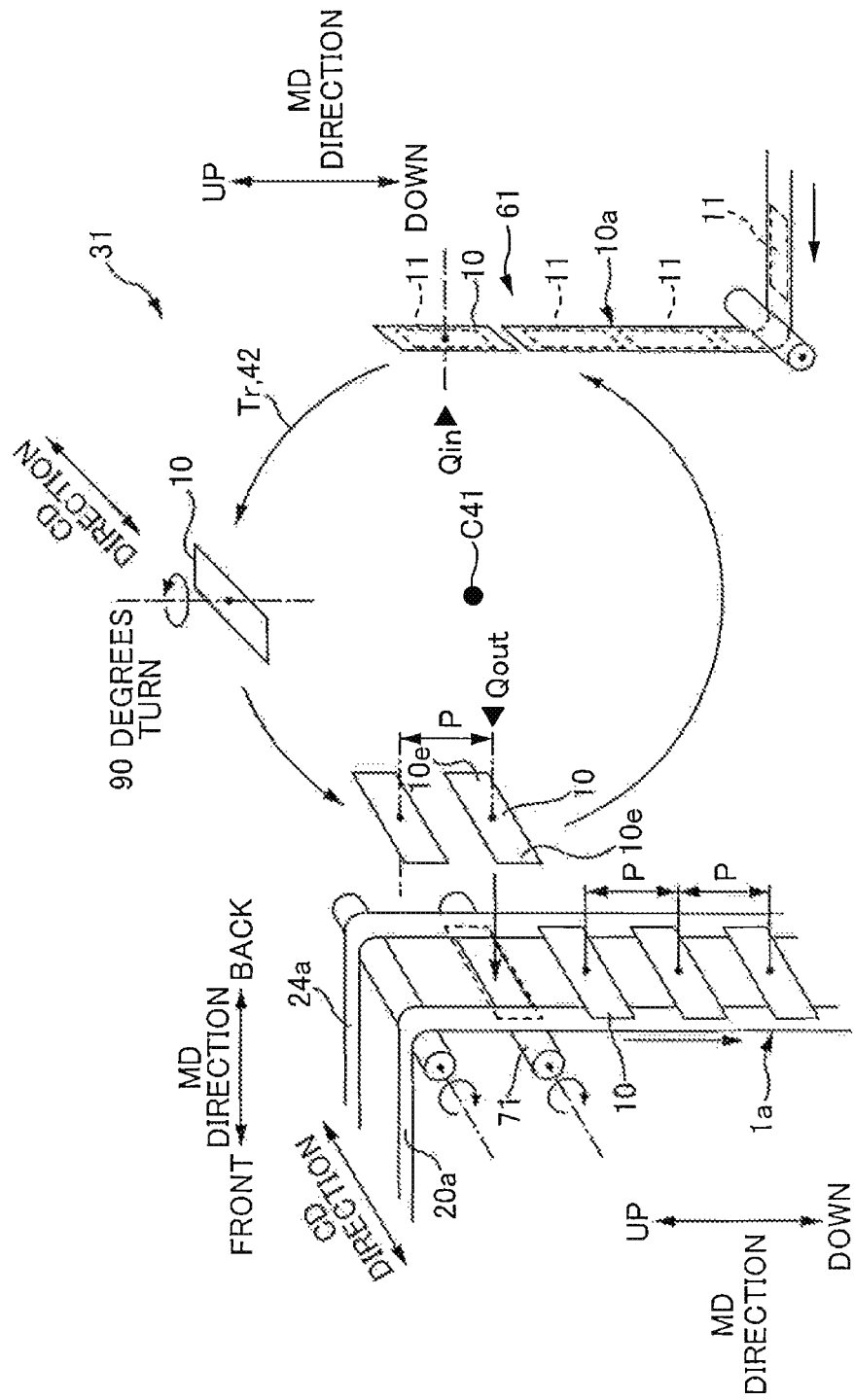
FIG. 4 is a schematic diagram of a process to be performed with manufacturing equipment 31 of the present embodiment.
Figure 5:
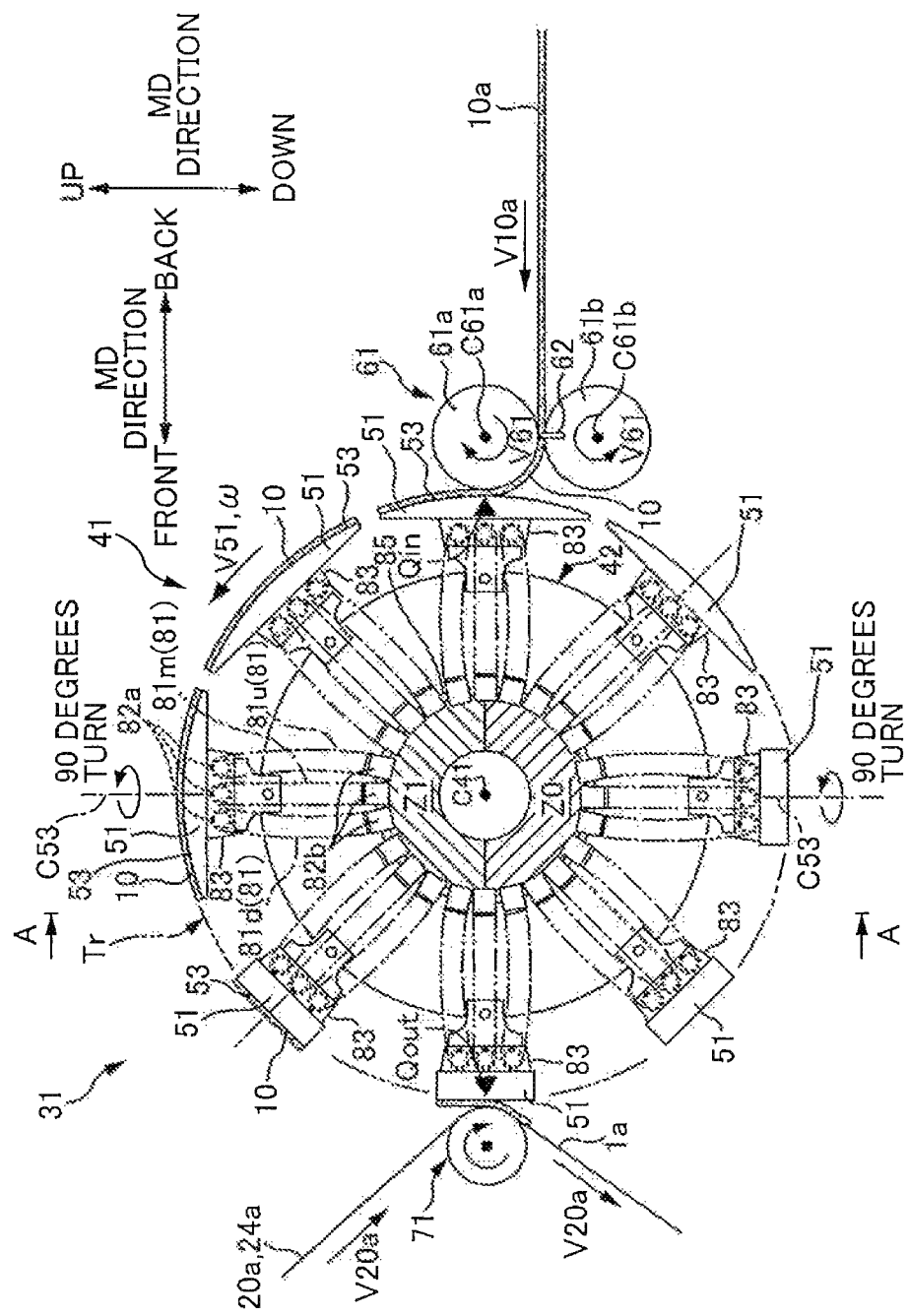
FIG. 5 is an illustrative picture of the manufacturing equipment 31 in this embodiment.

FIG. 4 is a schematic diagram of a process to be performed in this manufacturing equipment 31, and FIG. 5 is an illustrative picture of the manufacturing equipment 31. It should be noted that, hereinbelow, a width direction of manufacturing equipment 31 is referred to as a "CD direction", and a direction that intersects this CD direction is referred to as an "MD direction". In other words, the MD direction refers to any given direction in a plane that intersects with the CD direction. Further, in some cases, the 2 directions that intersect with each other in the MD direction may each be referred to as an "up-down direction" and a "front-back direction".

In this step, a process of putting the absorbent main body 10 over a pair of the belt members 20, 24 and adhering it thereto is performed, and thus a semifinished product of the diaper 1 becomes a substantially H-shape as shown in FIG. 1.

In more detail, as shown in FIG. 4, a pair of the belt members 20, 24 when being supplied to the manufacturing equipment 31 is being continuously transported in a form of continuous bodies 20a,24a along the MD direction, and in a state side by side with an .interval between each other in the CD direction. Further, the absorbent main body 10 is also continuously transported in a form of the continuous body 10a that continues in the MD direction. That is to say, the surface sheet member 12 and the back surface sheet member 13 configuring the absorbent main body 10 are in a state of continuous sheets that continue in a longitudinal direction of the absorbent main body 10, and the absorbent body 11 is interposed in between the surface sheet member 12 and back surface sheet member 13 and each absorbent body 11 is in a state arranged periodically in the longitudinal direction.

For this reason, with this manufacturing equipment 31, first, with a cutter device 61 (not shown in FIG. 4), the continuous body 10a of the absorbent main body is divided along the CD direction in a region in between the absorbent bodies 11, 11, and thus the absorbent main body 10 with the longitudinal direction facing the MD direction is formed. Then, a rotating drum 42 that drives and rotates around a center of axis C41 along the CD direction receives the absorbent main body 10 on a peripheral surface thereof, and in the process of moving the absorbent main body 10 from this receiving position (hereinbelow, referred to sis receiving position Qin) to a predetermined delivery position Qout with the drive rotation of the rotating drum 42, by turning the absorbent main body 10 90 degrees about a center of the plane, the longitudinal direction of the absorbent main body 10 is changed from the MD direction to the CD direction that is a parallel direction to the continuous bodies 20a, 24a of the belt member.

On the other hand, a transport roller 71 is arranged in the delivery position Qout, and a pair of the continuous bodies 20a, 24a of the belt member are wrapped around the transport roller 71 in the CD direction and continuously transported in the MD direction. Therefore, when the absorbent main body 10 passes by the delivery position Qout with the drive rotation of the rotating drum 42, both end sections 10e, 10e in the longitudinal direction of the absorbent main body 10 are adhered to the pair of continuous bodies 20a, 24a of the belt member. Thus, a semifinished product 1a of a substantially ladder shape in FIG. 4, which is a stage before the substantially H-shape in FIG. 1 described above, is formed.

Then, up to here is a processing range that this manufacturing equipment 31 is in charge of. By the way, in this example, the absorbent main body 10 corresponds to "the first sheet-like member", the pair of the continuous bodies 20a, 24a of the belt member corresponds to "the second sheet-like member", and the substantially ladder shaped semifinished product 1a corresponds to "the composite body of the sheet-like member of the absorbent article". Hereinbelow, each of the configuring elements 61, 41, 71 of this manufacturing equipment 31 are described.

<<<Cutter Device 61>>>

As shown in FIG. 5, the cutter device 61 has a pair of upper and lower rolls 61a, 61b that continuously drives and rotates in a predetermined peripheral speed V61 about center of axes C61a, C61b along the CD direction. The peripheral speed V61 is set at, for example, substantially a same speed as a transport velocity V10a of the continuous body 10a of the absorbent main body.

Here, the peripheral surface of the upper roll 61a is a smooth surface. Then, the upper roll 61a is arranged so that the peripheral surface thereof opposes the rotating drum device 41 so that it is closest in the receiving position Qin. Further, on the peripheral surface of the lower roll 61b is provided one flat blade 62 along the CD direction, and a perimeter of the peripheral surface is substantially the same as a length in design of the absorbent main body 10. Therefore, in the process the continuous body 10a of the absorbent main body is sent continuously in the MD direction with the drive rotation of these upper and lower rolls 61a, 61b, by the flat blade 62 of the lower roll 61b opposing the peripheral surface of the upper roll 61a and sandwiching the continuous body 10a of the absorbent main body, the absorbent main body 10 for the length part in design is divided and formed in a front end side of this continuous body 10a.

It should be noted that, with the upper roll 61a, a plurality of suction holes (not shown) are included on its peripheral surface. Then, in respect to a circumferential direction of the upper roll 61a, suction operation with these suction holes is performed at all times over a range from a position closest to the lower roll 61b to a position opposing the receiving position Qin. Therefore, the absorbent main body 10 that is divided and formed, and a front end section of the continuous body 10a that has been newly formed by dividing are both firmly sucked and held on the peripheral surface of the upper roll 61a and surely sent to the receiving position Qin of the rotating drum device 41.

<<<Rotating Drum Device 41>>>

The rotating drum device 41 includes the rotating drum 42 that drives and rotates about the center of axis C41 along the CD direction and a plurality of sheets (8 sheets in the example shown) of the workpiece holding pallets 51 (corresponds to holding sections) supported side by side in equal pitch in the circumferential direction of the peripheral surface of the rotating drum 42 in order to hold the absorbent main bodies 10.

The rotating drum 42 is a substantially cylindrical member, and drives and rotates in a predetermined angular velocity ω for example in one direction counterclockwise with an appropriate motor and the like as a driving source. Then, as a result each of the workpiece holding pallets 51 moves on a perfect circle shape trajectory Tr with the center of axis C41 as the center of the circle in a predetermined moving velocity V51 based on the angular velocity ω.

On this trajectory Tr are set the above-described receiving position Qin and the delivery position Qout. Therefore, in the receiving position Qin, each of the workpiece holding pallets 51 receives the absorbent main body 10 from the cutter device 61, and in the delivery position Qout, in cooperation with the transport roller 71 in the same position Qout, the absorbent main body 10 on the workpiece holding pallet 51 is bonded and delivered to the pair of the continuous bodies 20a, 24a of the belt member.

Figure 6A:
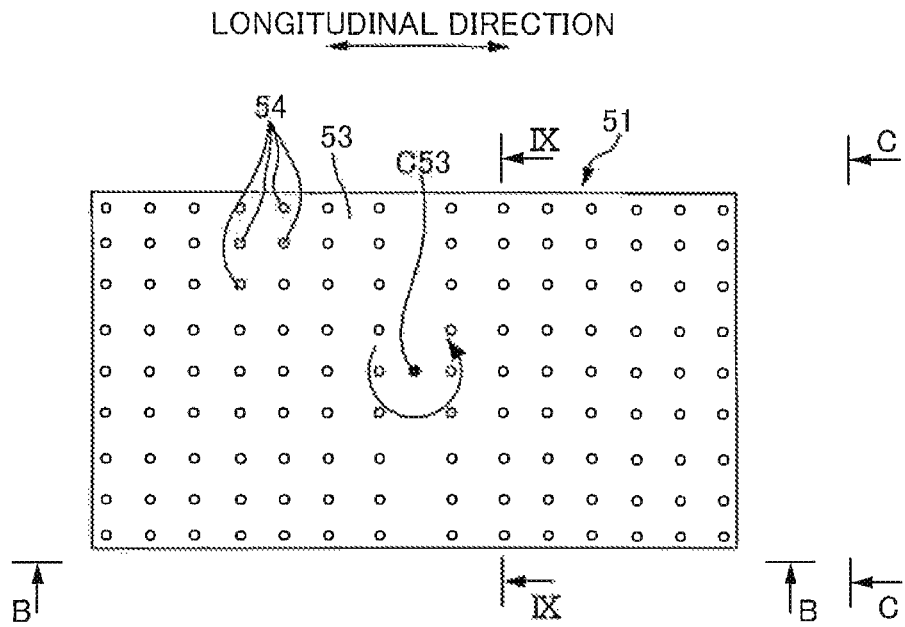
FIG. 6A is a front view of a workpiece holding pallet 51.
Figure 6B:
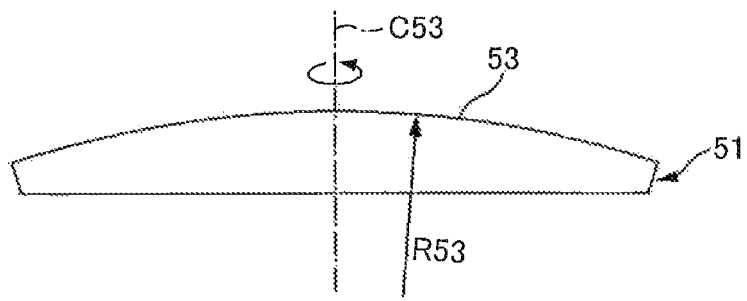
FIG. 6B is a B-B arrow view in FIG. 6A.
Figure 6C:
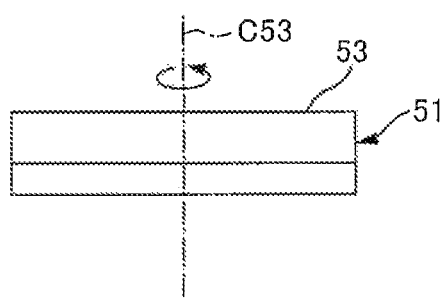
FIG. 6C is a C-C arrow view in FIG. 6A.

FIG. 6A is a front view of the workpiece holding pallet 51, FIG. 6B is a B-B arrow view in FIG. 6A, and FIG. 6C is a C-C arrow view in FIG. 6A.

The workpiece holding pallet 51 is a substantially rectangular shaped plate shaped member having a holding surface 53 that holds the absorbent main body 10 in a surface contacting state, and as shown in FIG. 5 the holding surface 53 is faced toward the outside in the rotating radius direction of the rotating drum 42. As shown in FIG. 6A, on the holding surface 53 is formed with a plurality of suction holes 54 (corresponds to holes) over substantially the entire surface thereof, and these suction hole 54 are connected to a negative pressure zone Z1 to be described later via a suction chamber 56 and a duct such as a suction pipe 81 inside the workpiece holding pallet 51. Therefore, with the suction air from these suction holes 54, suction force to hold the absorbent main body 10 is generated on the holding surface 53. This suction operation is performed over a range from the receiving position Qin to the delivery position Qout in FIG. 5, and is generally stopped in other ranges. It should be noted that, this suction operation is to be described later.

Further, the longitudinal direction of the holding surface 53 is aligned with the longitudinal direction of the workpiece holding pallet 51. Therefore, as will be described later, in the case the longitudinal direction of the workpiece holding pallet 51 in the receiving position Qin is made to face the MD direction, the absorbent main body 10 that is sent from the cutter device 61 in a state the longitudinal direction is facing the MD direction can be held firmly with the holding surface 53. Furthermore, as shown in FIG. 6A, the holding surface 53 is formed in an arc shape in section along the longitudinal direction, and its radius of curvature R53 is substantially a same value as a rotating radius of si trajectory Tr in FIG. 5. Therefore, a moving velocity V51 of the workpiece holding pallet 51 in the receiving position Qin can be maintained at a constant velocity over the entire length in the longitudinal direction of the workpiece holding pallet 51. Therefore, in the case an angular velocity ω of the rotating drum 42 is set so that the moving velocity V51 of the workpiece holding pallet 51 is the same as a transport velocity V10a of the continuous body 10a of the absorbent main body, the workpiece holding pallet 51 can receive the absorbent main body 10 that is sent from the cutter device 61 in an extended state almost without any creases over its entire length.

Further, as shown in FIG. 5 to FIG. 6C, the workpiece holding pallet 51 is turnable about a turning center of axis C53 that passes si center on a plane of the holding surface 53 and is along a rotating radius direction of the rotating drum 42. Therefore, by the workpiece holding pallet 51 being turned around this turning center of axis C53, the absorbent main body 10 on the workpiece holding pallet 51 also turns together with the workpiece holding pallet 51, and thus the longitudinal direction of the absorbent main body 10 is changed from the MD direction to the CD direction. Then, after delivering the absorbent main body 10 in the delivery position Qout, the workpiece holding pallet 51 turns 90 degrees again in order to receive the absorbent main body 10 in the receiving position Qin, and thus the longitudinal direction of the workpiece holding pallet 51 is returned from the CD direction to the MD direction. An appropriate motor and the like can be given as a driving source of this turning operation.

<<<Transport Roller 71>>>

Figure 7A:
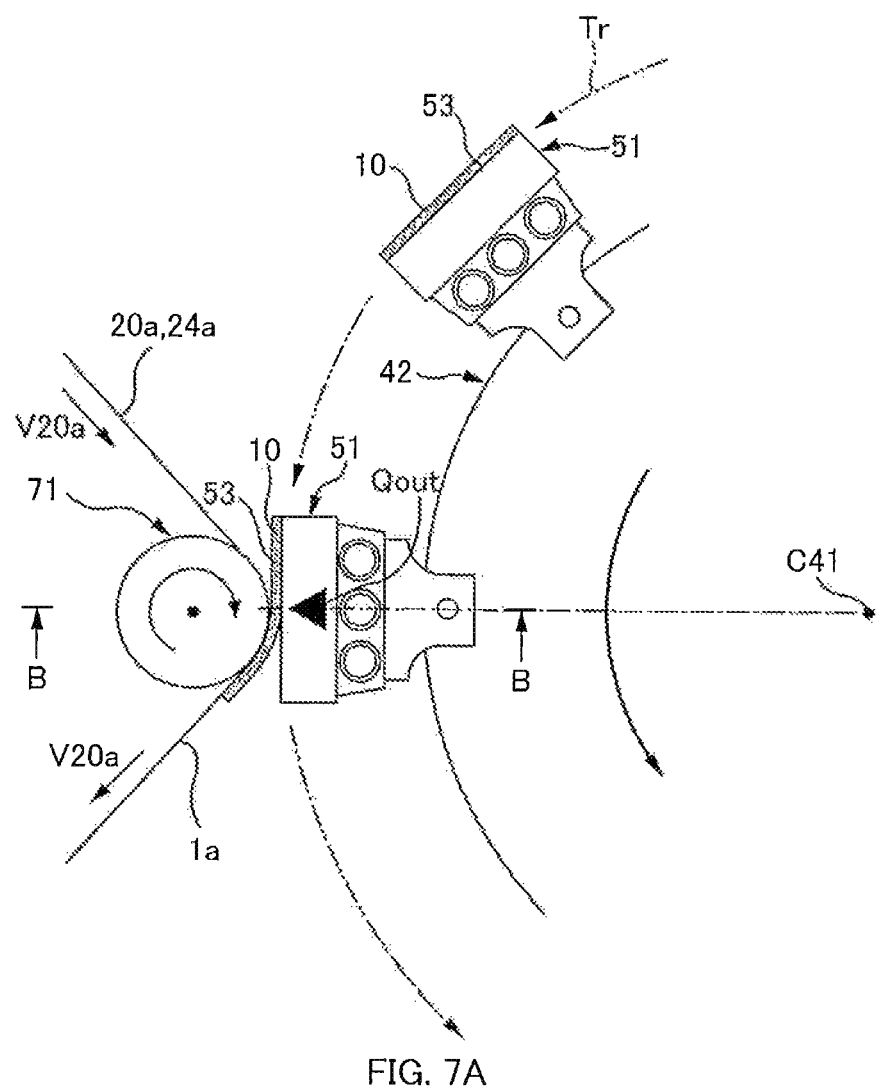
FIG. 7A is an enlarged view of a transport roller 71.
Figure 7B:
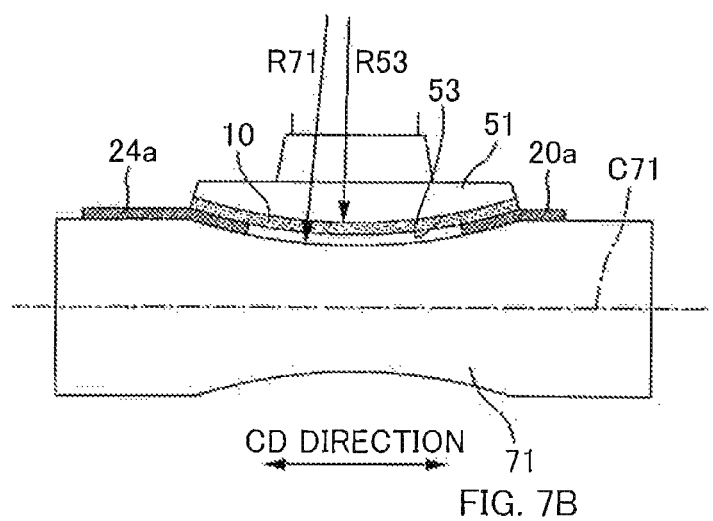
FIG. 7B is a B-B cross section view in FIG. 7A.

FIG. 7A is an enlarged view of a transport roller 71 arranged in the delivery position Qout, and FIG. 7B is a B-B cross section view in FIG. 7A. The transport roller 71 is a follower roller 71 that is rotatably supported around the center of axis C71 facing the CD direction. A pair of continuous bodies 20a, 24a of the belt member is wrapped around the peripheral surface of the transport roller 71 and is made to follow and rotate with the travel of the continuous bodies 20a, 24a. It should be rioted that, a traveling velocity V20a (transport velocity) of the pair of the continuous bodies 20a, 24a of the belt member is set at approximately a same value as the moving velocity V51 of the workpiece holding pallet 51 of the rotating drum 42.

As shown in FIG. 7B, an external shape of the transport roller 71 is in a shape that is concave in a central section in the CD direction, in correspondence with a convex shape (FIG. 6B) of the holding surface 53 of the workpiece holding pallet 51. In more detail, in the delivery position Qout the longitudinal direction of the workpiece holding pallet 51 is facing the CD direction, and further the shape of the holding surface 53 of the workpiece holding pallet 51 is in an arc shape in which the central section bulges outward more than the both end sections in the longitudinal direction in a rotating radius direction of the rotating drum 42, as described above. Therefore, in correspondence with this arc shape, the shape of the peripheral surface of the transport roller 71 is set in an arc shape with a roll curve in which a radius of the transport roller 71 gradually becomes smaller from the end sections in the CD direction to the central section. Then, as a result of this, the transport roller 71, with the workpiece holding pallet 51 passing the delivery position Qout, sandwiches the absorbent main body 10 over an entire length in its CD direction substantially equally and can surely hold the absorbent main body 10.

Here preferably, a radius of curvature R71 of this roll curve is made equal to or greater than the radius of curvature R53 of the arc shape of the workpiece holding pallet 51, and equal to or smaller than 1.2 times the radius of curvature R53, and more preferably, to a radius of curvature greater than the radius of curvature R53. In this way, the holding surface 53 and the transport roller 71 can be prevented from strongly contacting locally the absorbent main body 10 in both end sections in the CD direction, and as a result the damage the absorbent main body 10 may receive can be lessened. It should be noted that, as a guideline in the case of setting the radius of curvature R71 greater than the radius of curvature R53 described above, for example, such as making the radius of curvature greater for an amount of thickness in design of the absorbent main body 10 can be given.

As a material of the transport roller 71, a flexible material that elastically deforms at least in a peripheral section with a contact pressure when the workpiece holding pallet 51 is contacted is preferable, and as one example thereof there can be given a sponge form polyurethane rubber and the like. Then, by using such a material, during delivery the absorbent main body 10 that is sandwiched with the workpiece holding pallet 51 and the transport roller 71 can be prevented from being largely damaged.

<<<Delivery Operation of Absorbent Main Body 10 in Delivery Position Qout>>>

FIG. 8A to FIG. 8E are illustrative pictures of the manner of delivery of the absorbent main body 10 that is performed in the delivery position Qout.

As described above, on the peripheral surface of the transport roller 71 in the delivery position Qout, the pair of continuous bodies 20a, 24a of the belt member are wrapped around and continuously transported, and a part of the peripheral surface of the transport roller 71 is positioned in the delivery position Qout on the trajectory Tr. On the other hand, the holding surface 53 of the workpiece holding pallet 51 also passes by the delivery position Qout along the trajectory Tr.

Then, when each of the sections of the absorbent main body 10 that has been held on the holding surface 53 passes by the delivery position Qout, each of the sections subsequently adheres to the pair of continuous bodies 20a, 24a of the belt member on the peripheral surface of the transport roller 71 and is delivered to the continuous bodies 20a, 24a. Therefore, this delivery operation takes on the semblance of transfer to a curved surface along the peripheral surface of the transport roller 71, in other words, a so-called curved surface transfer.

Here, in the case of this curved surface transfer, the delivery operation of the absorbent main body 10 from the holding surface 53 to the pair of continuous bodies 20a, 24a of the belt member is not performed simultaneously over the entire surface of the holding surface 53, and is performed so that an area in which the absorbent main body 10 is delivered to the holding surface 53 is sequentially shifted from a downstream side to an upstream side in the trajectory Tr. That is to say, the delivering timing is shifted between at least an area 55d in the downstream side of the holding surface 53 (hereinbelow, also referred to as a downstream side area) and an area 55u in the upstream side (hereinbelow, also referred to as an upstream side area). In other words, the absorbent main body 10 can be said to include a section to be delivered first (a section to be held in a downstream side area 55d) and a section to be delivered subsequently (a section to be held in an upstream side area 55u).

Figure 9:
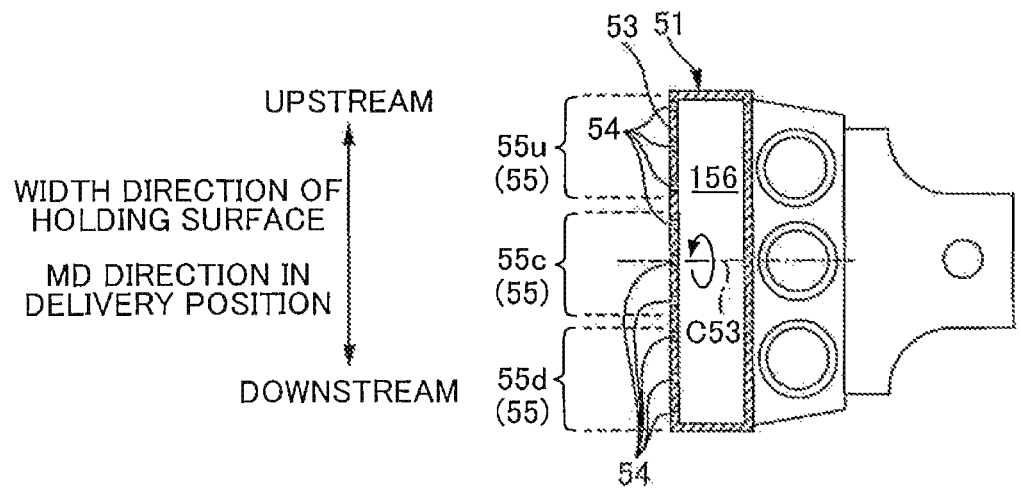
FIG. 9 is an illustrative picture of a general example of a holding surface 53 of a suction configuration and is a cross section view corresponding to a diagram of a IX-IX section in FIG. 6A.

On the other hand, there is given as a general example of a suction configuration of the holding surface 53, as shown in a cross section view in FIG. 9 (corresponds to a cross section view in IX-IX section in FIG. 6A), just one substantially closed space in a negative pressure state that is partitioned and formed as a suction chamber 156 inside the workpiece holding pallet 51, and this suction chamber 156 is in communication with all the suction holes 54 on the holding surface 53 so as to allow air to pass through.

However, in the case that the above-described curved surface transfer is performed with such a suction configuration, the suction force on the holding surface 53 decreases in a latter half of the delivery operation, and the absorbent main body 10 cannot be held firmly, and there is a possibility that the delivery operation cannot be performed accurately.

Figure 8A:
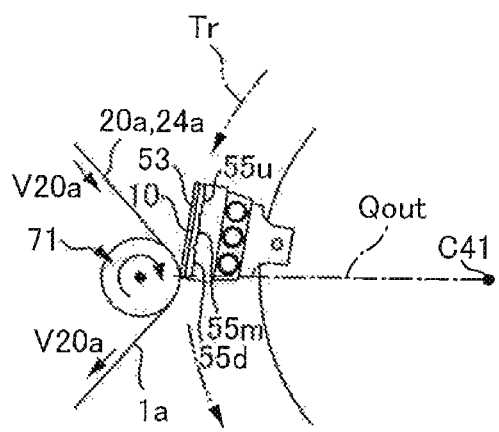
FIG. 8A to FIG. 8E are illustrative pictures of delivery situations of an absorbent main body 10 to be performed at a delivery position Qout.
Figure 8D:
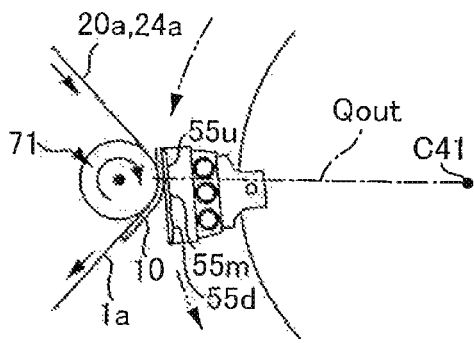
Figure 8B:
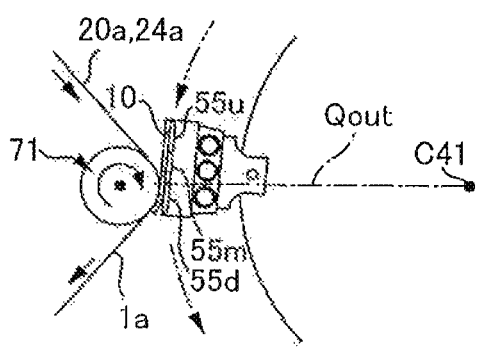
Figure 8E:
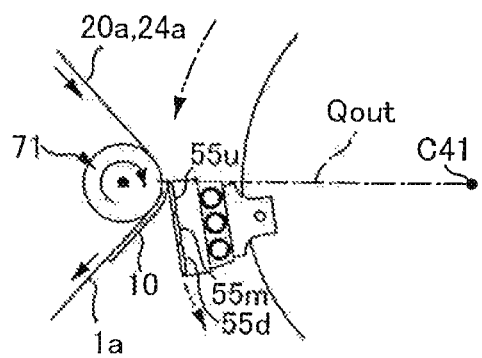
Figure 8C:
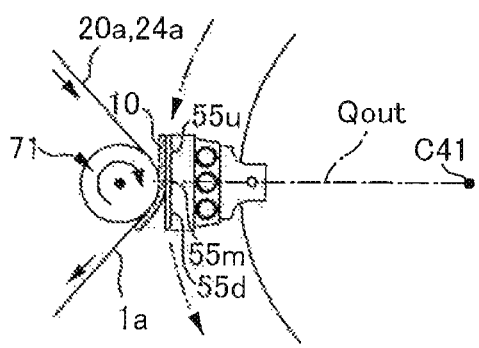

In more detail, first, before delivery in FIG. 8A, and in the case the downstream side area 55d of the holding surface 53 is just delivering the absorbent main body 10 as shown in FIG. 8B, the holding surface 53 is covered with the absorbent main body 10 over substantially an entire area thereof, therefore the absorbent main body 10 is firmly held with a predetermined level of suction force over the entire area of tire holding surface 53. However, as in FIG. 8C and FIG. 8D, in the case the downstream side area 55d on the holding surface 53 has passed by the delivery position Qout, and the upstream side area 55u on the holding surface 53 has started to pass by the delivery position Qout, the section of the absorbent main body 10 corresponding to the downstream side area 55d has already been delivered to the continuous bodies 20a, 24a of the belt member, so that at this point the downstream side area 55d is not covered by the absorbent main body 10.

Then, the suction holes 54 of this downstream side area 55d take the lead to suck in a large amount of outside air in a state in which it can sack with a small suction resistance, and a negative pressure level of the suction chamber 156 increases to an extreme. As a result, the suction force of the suction holes 54 in the upstream side area 55u of the holding surface 53 becomes small, and the holding property of the upstream side area 55u significantly decreases. Then, due to the above, the section corresponding to the upstream side area 55u of the absorbent main body 10 is deformed or the like before being delivered, and there is a possibility that the attaching precision to the pair of continuous bodies 20a, 24a of the belt member decreases.

Figure 10:
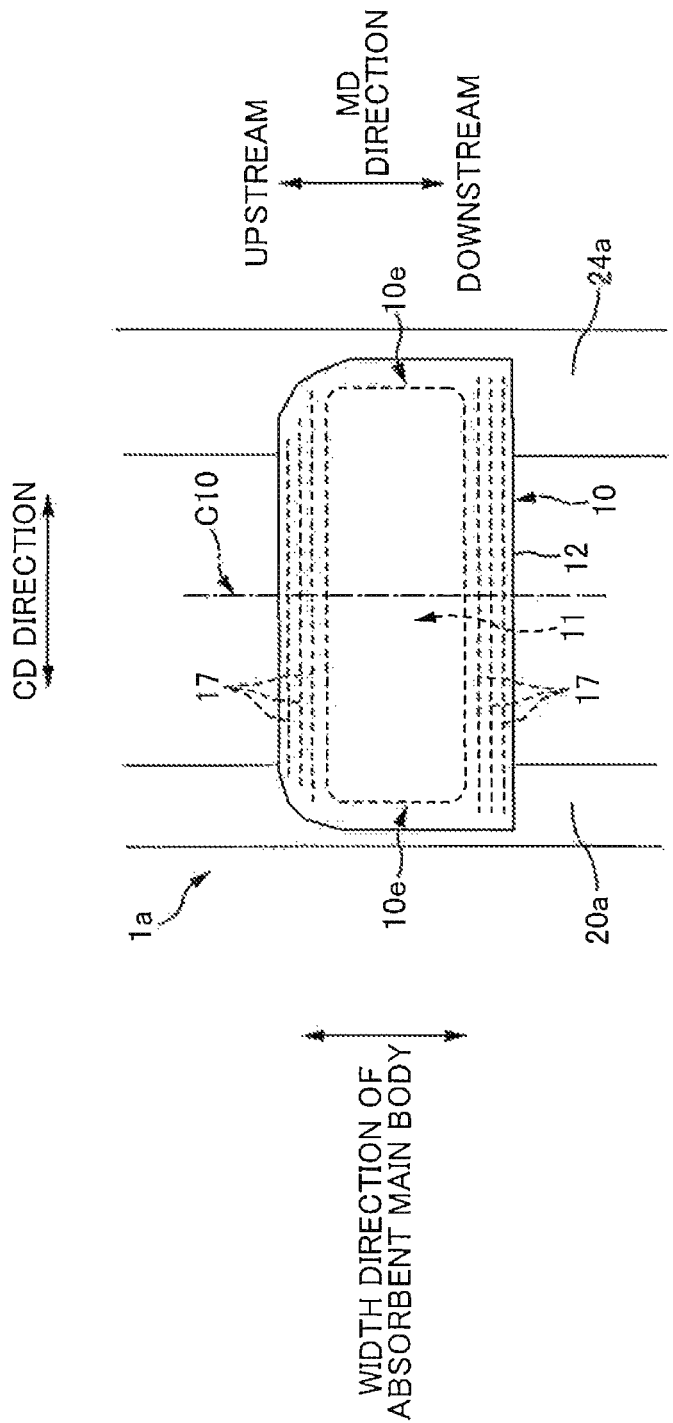
FIG. 10 is an illustrative picture of a problem that may occur in a suction configuration in a general example.

For example, as described above, the both end sections in the width direction of the absorbent main body 10 in FIG. 1 are fixed with an elastic member 17 to form an around-leg gather section, and in the state the absorbent main body 10 is held on the holding surface 53, the elastic member 17 is in a state extended in the longitudinal direction of the absorbent main body 10. Therefore, in a latter half of a series of the delivery operations, in the case the suction force of the upstream side area 55u of the holding surface 53 shown in FIG. 9 decreases, one end section in the width direction of the absorbent main body 10 to be sucked and held with the upstream side area 55u cannot go against contractive force of the elastic member 17 and contracts in the longitudinal direction. As a result, as shown in FIG. 10 the absorbent main body 10 is adhered to the pair of the continuous bodies 20a, 24a of the belt member in an asymmetrical shape in the width direction.

Figure 11A:
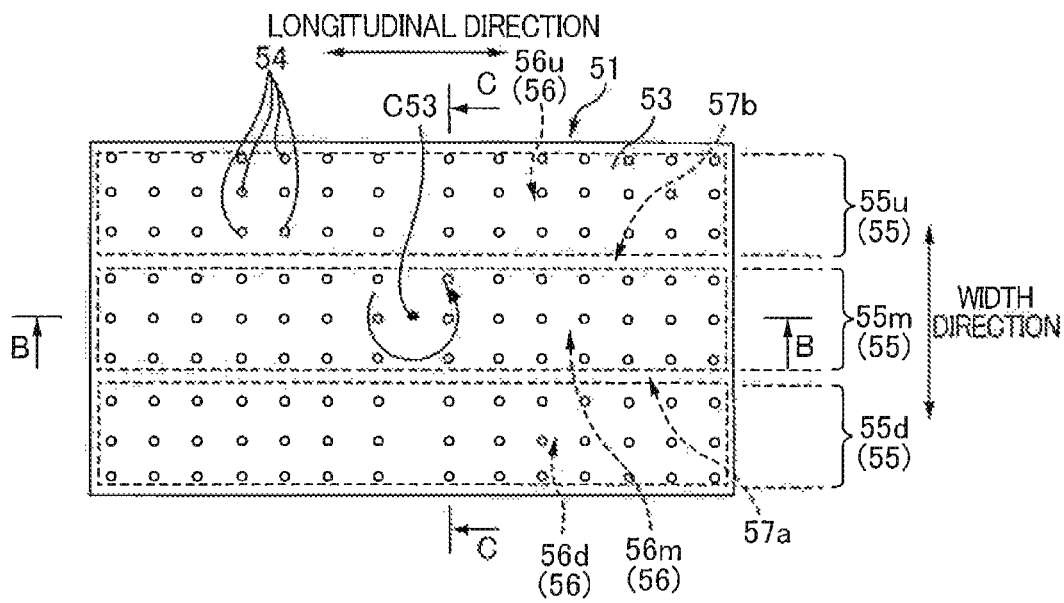
FIG. 11A is a plan view showing a division of a suction area 55 of the workpiece holding pallet 51 of this embodiment.
Figure 11B:
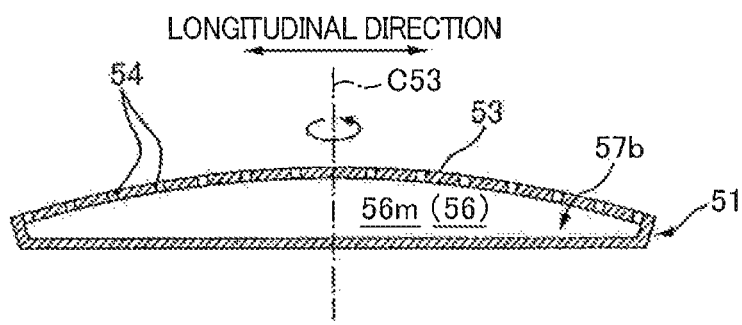
FIG. 11B is a B-B cross section view in FIG. 11A.
Figure 11C:
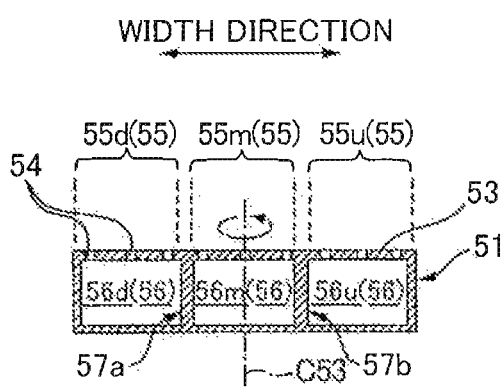
FIG. 11C is a C-C cross section view in FIG. 11A.

Then, in this embodiment, the holding surface 53 of the workpiece holding pallet 51 is divided into two of at least the upstream side area 55u and the downstream side area 55d, and suction chambers 56u, 56d are provided for each of the areas 55u, 55d inside the workpiece holding pallet 51, and these suction chambers 56u, 56d are partitioned so as not to allow air through to each other (refer to FIG. 11A to FIG. 11C). Then, in this way, the areas are divided so the suction air state of the suction holes 54 in the downstream side area 55d of the holding surface 53 do not affect the suction holes 54 in the upstream side area 55u, and as a result the decrease in the suction force of the upstream side area 55u of the holding surface 53 that may occur in the latter half of the delivery operation can be prevented.

FIG. 11A is a plan view showing a division of an area 55 of the workpiece holding pallet 51 of this embodiment, FIG. 11B is a B-B cross section view in FIG. 11A, and FIG. 11C is a C-C cross section view in FIG. 11A.

As shown in FIG. 11A, the holding surface 53 of the workpiece holding pallet 51 is divided into three areas 55 in its width direction. In other words, the holding surface 53 is divided into the downstream side suction area 55d positioned in a downstream side of the trajectory Tr when delivering, the upstream side suction area 55u positioned in an upstream side than this downstream side suction area 55d, and the middle suction area 55m positioned in between these suction areas 55d, 55u.

Then, corresponding to each of the suction areas 55d, 55m, 55u, inside the workpiece holding pallet 51 three suction chambers 56 are partitioned with an approximately equal capacity to each other, and in a chamber form that does not allow air to pass through to each other (in a state surrounded by wall sections from all directions in the space). In more detail, in the internal space of the workpiece holding pallet 51, two division walls 57a, 57b along the longitudinal direction of the holding surface 53 are arranged side by side to each other in the width direction, and the three suction chambers 56 are separated from each other by these division walls 57a, 57b so as not to allow air to pass through to each other. Further, these three suction chambers 56, namely, the downstream side suction chamber 56d (corresponds to a first suction chamber), the middle suction chamber 56m (corresponds to a third suction chamber), and the upstream side suction chamber 56u (corresponds to a second suction chamber) are each connected with exclusive suction pipes 81d, 81m, 81u via a middle chamber member 83 to be described later (refer to FIG. 12B), and each suction pipe 81d, 81m, 81u is configured to be able to independently suck out air in each corresponding suction chamber 56. Therefore, it is possible to make the pressure state in each suction chamber 56d, 56m, 56u to be in a completely divided state so that it does not affect each other, and thus the holding surface 53 can surely hold the absorbent main body 10 from the beginning to the end of the delivery operation. It should be noted that, hereinbelow, a suction pipe for the downstream side suction chamber 56d is also referred to as a downstream side suction pipe 81d, and a suction pipe for the middle suction chamber 56m is also referred to as a middle suction pipe 81m, and a suction pipe for the upstream side suction chamber 56u is also referred to as an upstream side suction pipe 81u.

Here, preferably, each of the suction areas 55d, 55m, and 55u stops and weakens suction independently from each of the other suction areas 55, in correspondence to the delivery operation of the section of the absorbent main body 10 that each area is in charge of. That is to say, in the case that each of the suction areas 55 of the downstream side suction area 55d, the middle suction area 55m, and the upstream side suction area 55u passes by the delivery position Qout, each of the suction areas 55d, 55m, and 55u may stop suction of its own area independently of the other suction areas 55. In other words, each of the suction areas 55d, 55m, 55u, when sandwiching the pair of the continuous bodies 20a, 24a of the belt member with the transport roller 71 and contacting the transport roller 71, may stop suction of its own area independently of the other suction areas 55.

Then, in this way, the section of the absorbent main body 10 to be delivered from being continually sucked onto each suction area 55 and being inhibited from being delivered can be prevented in advance. As a result, delivery from each of the suction areas 55 can be performed smoothly. By the way, it is needless to say that the suction operation of the suction area 55 that has been stopped is restarted in the case that the workpiece holding pallet 51 that such a suction area 55 belongs to passes by the receiving position Qin.

Figure 12A:
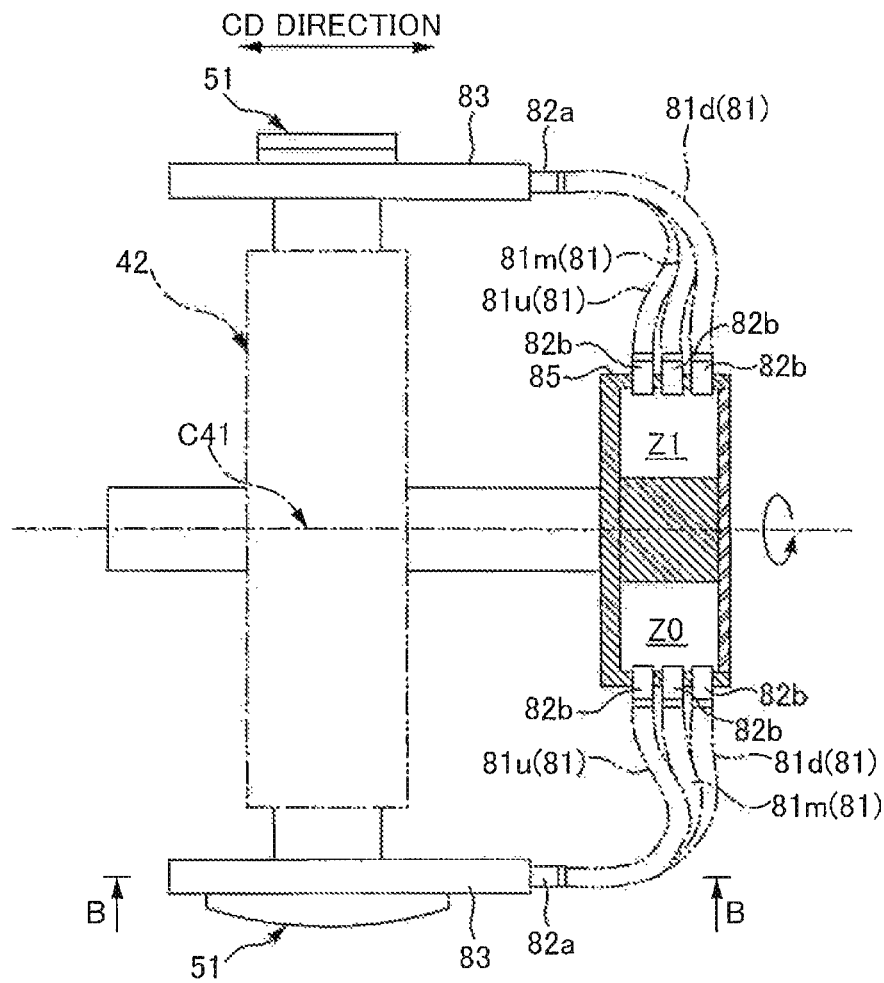
FIG. 12A is an A-A arrow view in FIG. 5.
Figure 12B:
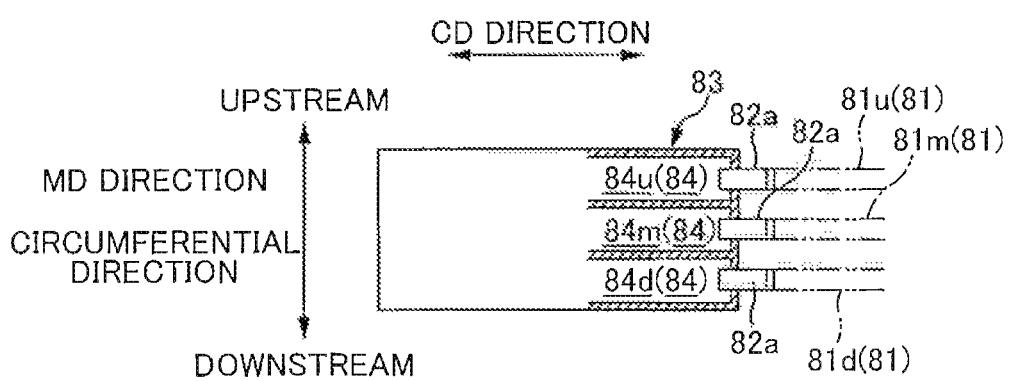
FIG. 12B is a B-B cross section view in FIG. 12A.

As one example of a suction air configuration that can independently stop the suction operation subsequently in units of the suction area 55, in response to the delivery operation of each of the suction areas 55d, 55m, 55u in this way, there is given a configuration such as that shown in FIG. 12A and FIG. 12B. FIG. 12A is an A-A arrow view in FIG. 5, and FIG. 12B is a B-B cross section view in FIG. 12A. It should be noted that, in FIG. 12A, a negative pressure chamber drum 85 to be described later is shown in a central vertical section view.

As shown in FIG. 5 and FIG. 12A, this suction air configuration has the negative pressure chamber drum 85 that has a part of an internal space that has been set as a negative pressure zone Z1, as a negative pressure source, and a middle chamber member 83 that has been arranged for each workpiece holding pallet 51 opposing the workpiece holding pallet 51 in a position to an inner side in the rotating radius direction of the rotating drum 42 than the workpiece holding pallet 51, in order to relay between the negative pressure chamber drum 85 and the suction chamber 56 of the workpiece holding pallet 51. Then, each middle chamber member 83 is in communication with the internal space of the negative pressure chamber drum 85 with the above-described three suction pipes 81 provided for each of the middle chamber member 83, and thus each middle chamber member 83 performs the suction operation of the workpiece holding pallet 51 that each is in charge of.

In more detail, as shown in FIG. 12B, the internal space of the middle chamber member 83 is partitioned into three substantially closed chambers 84. Each chamber 84 is formed with a substantially equal capacity to each other, and is each corresponded to any one of the downstream side suction chamber 56d, the middle suction chamber 56m, and the upstream side suction chamber 56u in the workpiece holding pallet 51. In other words, each chamber 84 is connected so as to allow air to pass through with one end opening 82a of one corresponding suction pipe 81 out of the three suction pipes 81.

Then, in a state in which the longitudinal direction of the workpiece holding pallet 51 is facing the MD direction, each chamber 84 is in communication with all the suction chambers 56d, 56m, 56u, but on the contrary, in a state in which the longitudinal direction is facing the CD direction, each chamber 84 is configured so as to be in communication with only the corresponding suction chamber 56. Therefore, in a state the longitudinal direction of the workpiece holding pallet 51 is facing the MD direction, all three suction pipes 81d, 81m, 81u cooperate to perform the suction operation of each suction chamber 56, and in a state in which the longitudinal direction of the workpiece holding pallet 51 is facing the CD direction, the suction operation of each suction chamber 56 is performed with only one corresponding suction pipe 81. In other words, the suction operation of the downstream side suction chamber 56d is performed with only the downstream side suction pipe 81d, the suction operation of the middle suction chamber 56m is performed with only the middle suction pipe 81m, and the suction operation of the upstream side suction chamber 56u is performed with only the upstream side suction pipe 81u. As a result, the suction operation of each of the suction areas 55d, 55m, 55u of the holding surface 53 in the delivery position Qout can be performed independently from each other.

On the other hand, as shown in FIG. 5 and FIG. 12A, the negative pressure chamber drum 85 has as a main body a cylindrical body that is arranged in parallel with a same core as the rotating drum 42 and that becomes integral with the rotating drum 42 and rotates at a same speed. A doughnut-shaped space inside the cylindrical body is divided into zones of a negative pressure zone Z1 and a non-negative pressure zone Z0 in a circumferential direction with an appropriate partition wail not shown. The negative pressure zone Z1 is connected to a decompressor such as a blower with an appropriate piping that is not shown, and is always maintained in a negative pressure state that is lower by a predetermined level than an outside atmospheric pressure. On the other hand, the non-negative pressure zone Z0 is maintained in an outside atmospheric pressure or a positive pressure that is slightly higher than the outside atmospheric pressure. Then, the negative pressure zone Z1 is set corresponding to an angle range from the receiving position Qin to the delivery position Qout, and the non-negative pressure zone Z0 is set corresponding to an angle range from the delivery position Qout to the receiving position Qin.

Further, to the peripheral wall section of the negative pressure chamber drum 85 is connected each of the other end opening 82b of the three suction pipes 81 for each workpiece holding pallet 51 (in other words, for each middle chamber member 83), each suction pipe 81 is made to communicate with the above-described negative pressure zone Z1 and the non-negative pressure zone Z0. Then, the connection positions of these other end openings 82b to the negative pressure chamber drum 85, as shown in FIG. 5, are arranged from the downstream side to the upstream side in the circumferential direction of the negative pressure chamber drum 85, subsequently, in order of the downstream side suction pipe 81d corresponding to the downstream side suction chamber 56d, the middle suction pipe 81m corresponding to the middle suction chamber 56m, and the upstream side suction pipe 56u corresponding to the upstream side suction chamber 56u, and are shifted in position in the circumferential direction to each other.

Accordingly, when the rotating drum 42 rotates, with the negative pressure chamber drum 85 that rotates integrally with the rotating drum each suction pipe 81 also moves around the perimeter of the negative pressure zone Z1 and the non-negative pressure zone Z0, and in such a case a timing that the other end opening 82b of the suction pipe 81 enters the non-negative pressure zone Z0 is shifted between each other of the three suction pipes 81d, 81m, 81u. Then, as a result in the case each suction area 55d, 55m, 55u passes by the delivery position Qout, the suction operation can be stopped by units of the suction area 55 subsequently arid independently of the order in which it passes. In other words, working together with the delivery operation of each of the suction areas 55d, 55m, 55u, the stopping of suction in units of the suction area 55 can be achieved.

It should be noted that, here preferably the non-negative pressure zone Z0 is made to be a positive pressure state higher than the outside atmospheric pressure. In this way, each suction area 55 that has passed by the delivery position Qin sequentially blows out air toward the absorbent main body 10 from the suction holes 54. That is to say, each suction area 55d, 55m, 55u shown m FIG. 8A to FIG. 8E, blasts air in order of the downstream side suction area 55d, the middle suction area 55m, and the upstream side suction area 55u, which is the order in which the suction operation was stopped. Thus, suction force that has a possibility of remaining even after passing the delivery position Qout can be ceased to exist completely, and delivering performance of the absorbent main body 10 to the continuous bodies 20a, 24a of the belt member can be greatly increased. Further, foreign matters such as fiber pieces that have adhered to the holding surface 53 of the workpiece holding pallet 51 can also be removed and purification performance becomes high, and also clogging of the suction holes 54 can be prevented in advance.

Figure 13A:
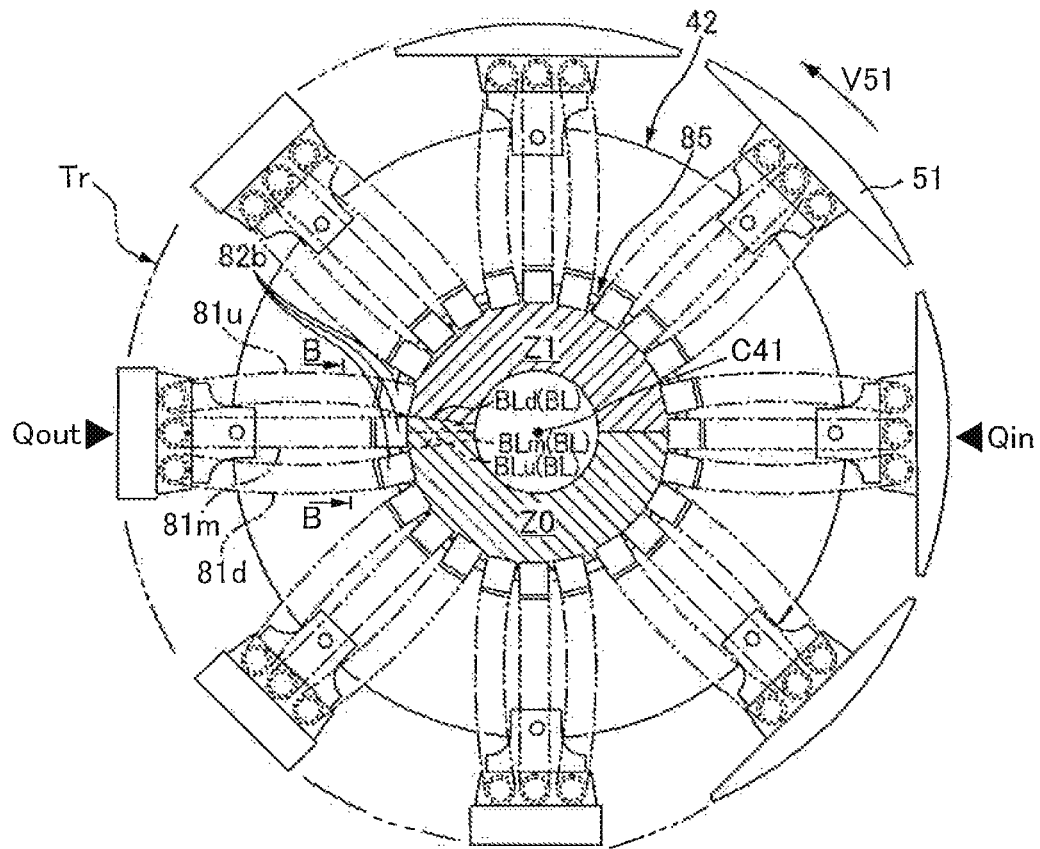
FIG. 13A is a preferable example of an illustrative picture of a connection position of the other end opening 82b of each suction pipe 81 to a negative pressure chamber drum 85.
Figures 13B, 13C:
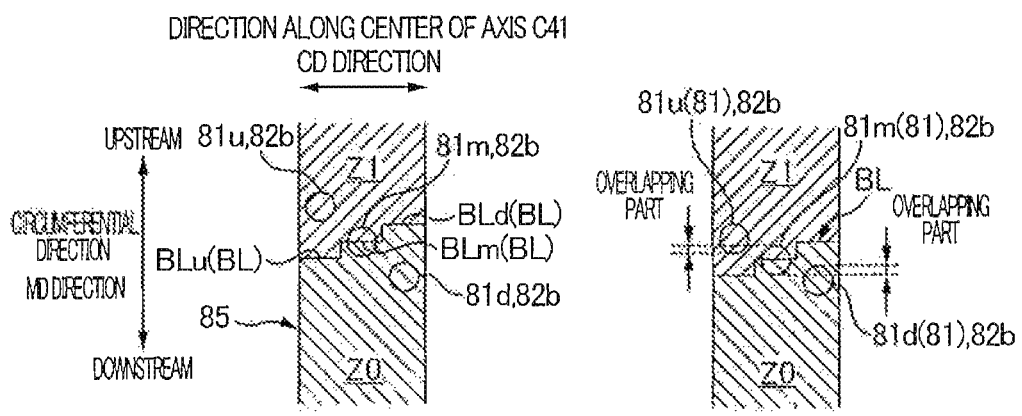
FIG. 13B is a B-B arrow view in FIG. 13A.
FIG. 13C is an illustrative picture of an effect of a preferable example of this connection position.

Further, preferably, as shown in FIG. 12A, the connection position of each suction pipe 81 to the other end opening 82b of the negative pressure chamber drum 85 is arranged shifted in respect to each other in a direction along a center of axis C41 of the rotating drum 42, and as shown in FIG. 13A and FIG. 13B (a B-B arrow view in FIG. 13A), a boundary line BL of the negative pressure zone Z1 and the non-negative pressure zone Z0 is preferably positioned shifted in the circumferential direction of the negative pressure chamber drum 85 in respect to each other between each of the suction pipes 81d, 81m, 81u.

For example, in an example in FIG. 13E, in order of the downstream side suction pipe 81d, the middle suction pipe 81m, and the upstream side suction pipe 81u, the connection positions of each of the other end openings 82b is set side by side in a direction along the center of axis C41. Further, each boundary line BL of the suction pipes 81d, 81m, 81u are shifted in the circumferential direction m respect to each other in an order opposite to an aligning order in the circumferential direction of the other end openings 82b of the suction pipes 81d, 81m, 81u, in other words, the boundary line BLm for the middle suction pipe 81m is positioned in a downstream side than the boundary line BLd for the downstream side suction pipe 81d, further the boundary line BLu for the upstream side suction pipe 81u is positioned in the downstream side than the boundary line BLm, and an external shape of these boundary lines BL form a substantially step form.

Then, in this way, even in the case that it is difficult to physically ensure a connection space of multiple other end openings 82b on the peripheral wall surface of the negative pressure chamber drum 85, all the other end openings 82b can be connected without making the outside diameter size of the negative pressure chamber drum 85 large.

That is to say, in the above-described way, for example, as shown in FIG. 13C, even in the case that the connection positions of the three suction pipes 81d, 81m, 81u are partially overlapped and arranged in the circumferential direction of the negative pressure chamber drum 85, by the substantially step form boundary line BL, only the other end opening 82b of a particular suction pipe 81 can be selectively put in to the non-negative pressure zone Z0 from the negative pressure zone Z1. In other words, the three suction pipes 81d, 81m, 81u can be put in the non-negative pressure zone Z0 independently from each other. As a result, while ensuring independence of the suction operation of each of the suction pipes 81d, 81m, 81u, the negative pressure chamber drum 85 can be made small in diameter, and thus the power needed for driving arid rotating the negative pressure chamber drum 85 can be decreased. Further, freedom in design in size of the negative pressure chamber drum 85 can be increased.

===Other Embodiment Modes===

An embodiment mode of this invention is described above, but this invention is not limited to thereto, and modifications shown hereinbelow are also possible.

In the above-described embodiment mode, the workpiece holding pallet 51 is provided to the peripheral surface of the rotating drum 42, and the workpiece holding pallet 51 is moved in a trajectory Tr of a perfect circle shape, but it is not limited thereto, and it may be moved in a trajectory of a polygon shape such as a rectangle.

In the above-described embodiment mode, the diaper 1 in the mode in FIG. 2A was manufactured, but it is not limited thereto, and the diaper 1 in the mode in FIG. 2B can be manufactured using the manufacturing equipment 31 in FIG. 5. It should be noted that, in this case, the pair of the continuous bodies 20a, 24a of the belt member in the delivery position Qout is not transported in state in which the nonwoven fabric 21 is layered in two, and each continuous body 20a, 24a is transported in a one sheet state. Then, in the delivery position Qout, the absorbent main body 10 is adhered to the continuous bodies 20a, 24a of the belt member made of one sheet of the nonwoven fabric 21 to form a ladder form semifinished product. Then, in the below step of this manufacturing equipment 31, the continuous bodies 20a, 24a of the belt member made of one sheet of the nonwoven fabric is further joined to the semifinished product, and the continuous bodies 20a, 24a are adhered superimposed on the continuous bodies 20a, 24a of the belt member of the semifinished product and sandwiching each end section 0e, 10e in the longitudinal direction of the absorbent main body 10. As a result, a semifinished product of the diaper 1 corresponding to FIG. 2B is manufactured.

In the above-described embodiment mode, the disposable diaper 1 that absorbs excretory fluid such as urine as an absorbent article is illustrated, but it is not limited thereto, and it may be applied to manufacture of a sanitary napkin that absorbs excretory fluid such as menstrual blood.

In the above-described embodiment mode, three suction areas 55d, 55m, 55u are provided on the holding surface 53, and a total of three suction chambers 56d, 56m, 56u are partitioned inside the workpiece holding pallet 51 in correspondence to each suction area 55d, 55m, 55u, but as long as these numbers are a multiple, for example, the number of the suction area 55 and the number of the suction chamber 56 may be equal to or greater than two or four.

Figure 14:
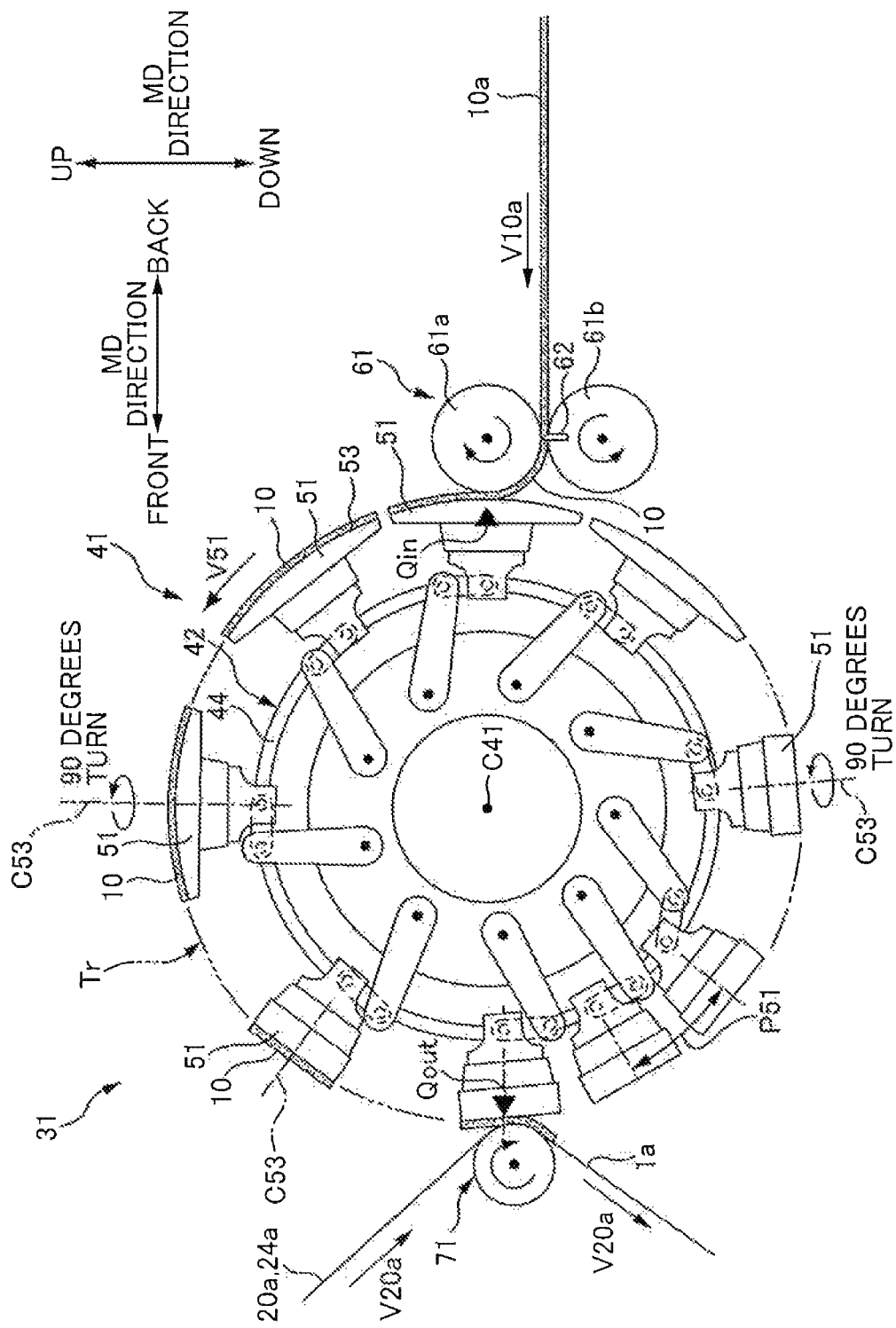
FIG. 14 is an illustrative picture of other embodiment modes of the manufacturing equipment 31.

In the above-described embodiment mode, the workpiece holding pallet 51 is fixed such that it cannot move relatively in the circumferential direction of the rotating drum 42 in respect to the rotating drum 42, but it is not limited thereto. For example, as shown in FIG. 14, each workpiece holding pallet 51 may be provided to be able to move reciprocatingly in the circumferential direction of the rotating drum 42 relatively in respect to the rotating drum 42. Then, in this case, since not only the rotating drum 42, but also each workpiece holding pallet 51 moves reciprocatingly, an orbiting operation on the trajectory Tr in an absolute coordinate system of each workpiece holding pallet 51 becomes a complex operation of a counterclockwise rotating operation of the rotating drum 42 itself combined with the reciprocating movement operation. Here, this complex operation may be allocated in correspondence to each rotation position on the trajectory Tr, and in that case the orbiting operation of the workpiece holding pallet 51 on the absolute coordinate system is to be performed based on a predetermined velocity pattern that is made by corresponding a moving velocity V51 in the circumferential direction to each rotation position. In other words, each workpiece holding pallet 51 repeats an orbiting operation based on a velocity pattern that has one 360 degrees rotation as one period. As a literature that has disclosed such a rotating drum device that can perform such a complex operation, Japanese Patent Application Laid-open Publication No. 2005-298193 can be illustrated.

In the above-described embodiment mode, the suction chambers 56d, 56m, 56u inside the workpiece holding pallet 51 are partitioned into a chamber form in a state that does not allow air to pass through each other at all times, but it is not limited thereto. In other words, as long as the absorbent main body 10 is configured to be able to be delivered to the pair of the continuous bodies 20a, 24a of the belt member, in a state in which the downstream side suction chamber 56d and the upstream side suction chamber 56u are partitioned so that air is not allowed to pass through to each other, the configuration can be other than that described above.

Figure 15A:
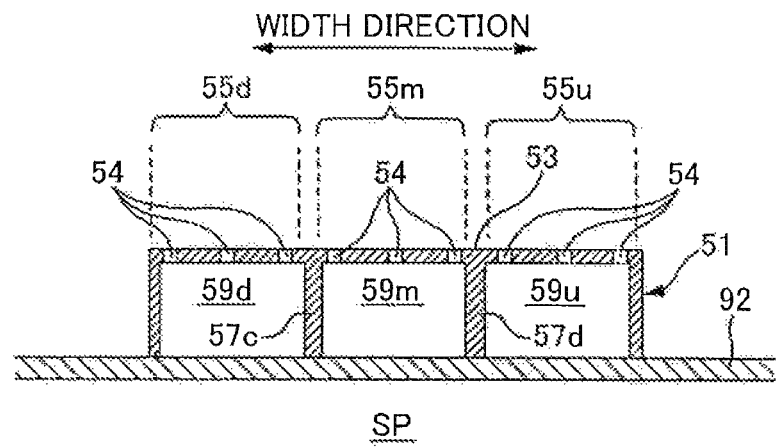
FIG. 15A to FIG. 15C are illustrative pictures of other embodiment modes.

For example, a configuration as shown in the cross section view in FIG. 15A is possible. That is to say, the workpiece holding pallet 51 has, instead of the above-described suction chamber 56, a recessed section that is in communication with the suction holes 54 of the holding surface 53 on the opposite surface to the holding surface 53. Further, this recessed section is divided into three recessed sections 59d, 59m, 59u with rib form division wails 57c, 57d, and each of the recessed sections 59d, 59m, 59u is corresponded to each of the suction areas 55d, 55m, 55u. Further, these three recessed sections 59d, 59m, 59u are covered with a movable wall 92, and thus are shielded from an adjacent negative pressure space SP.

Figure 15B:
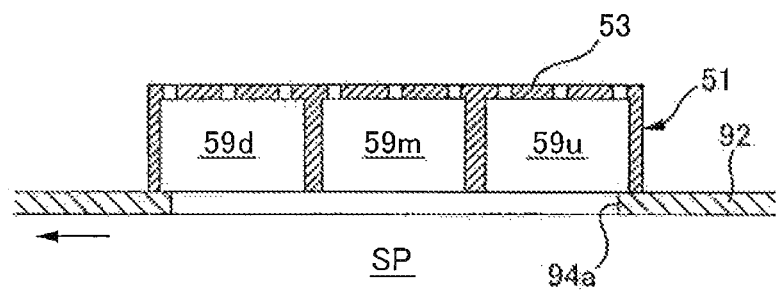

Then, in such a configuration, first, other than during delivering, as shown in FIG. 15B, by relative movement of the movable wall 92, all the recessed sections 59d, 59m, 59u are opposed to the same through hole 94a that has been formed through the movable wall 92 and made to be in communication with the negative pressure space SP, and thus the suction force is generated on the holding surface 53 of the workpiece holding pallet 51. Then, it can be said that each of the recessed sections 59d, 59m, 59u at this time is in a state in which air is allowed to pass through to each other.

Figure 15C:
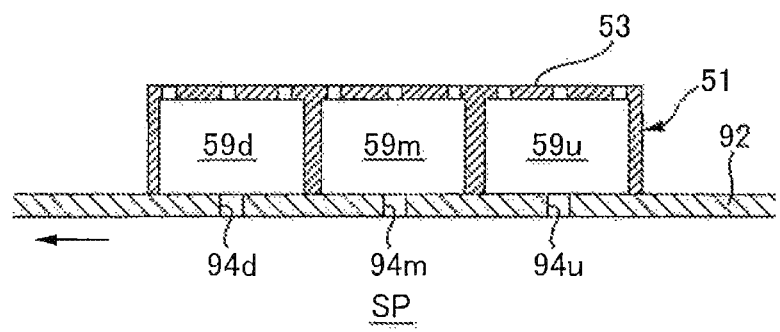

However, during delivery, with the relative movement of the movable wail 92, as shown in FIG. 15C, each of the recessed sections 59d, 59m, 59u is in a state opposed to each of the through holes 94d, 94m, 94u that have been formed through the movable wail 92 corresponding to each of these recessed sections 59*d*, 59*m*, 59*u*. Thus, each of the recessed sections 59*d*, 59*m*, 59*u* is made to be in communication with a negative pressure space SP via corresponding through holes 94*d*, 94*m*, 94*u*, and as a result, the suction force is generated on the holding surface 53 of the workpiece holding pallet 51. Then, each of the recessed sections 59*d*, 59*m*, 59*u* at this time are in a state partitioned so as not to allow air to pass through to each other, and thus decrease in the suction force of the upstream side area 55*u* of the holding surface 53 that may occur in the latter half of the delivery operation can be effectively prevented.

In the above-described embodiment mode, as shown in FIG. 11A to FIG. 11C the internal space of the workpiece holding pallet 51 is partitioned into the three suction chambers 56*d*, 56*m*, 56*u* in the width direction of the holding surface 53, but it is not limited thereto, and each of the suction chambers 56*d*, 56*m*, 56*u* may be further partitioned into a plurality of suction chambers 56 in the longitudinal direction of the holding surface 53.

Figure 16A:
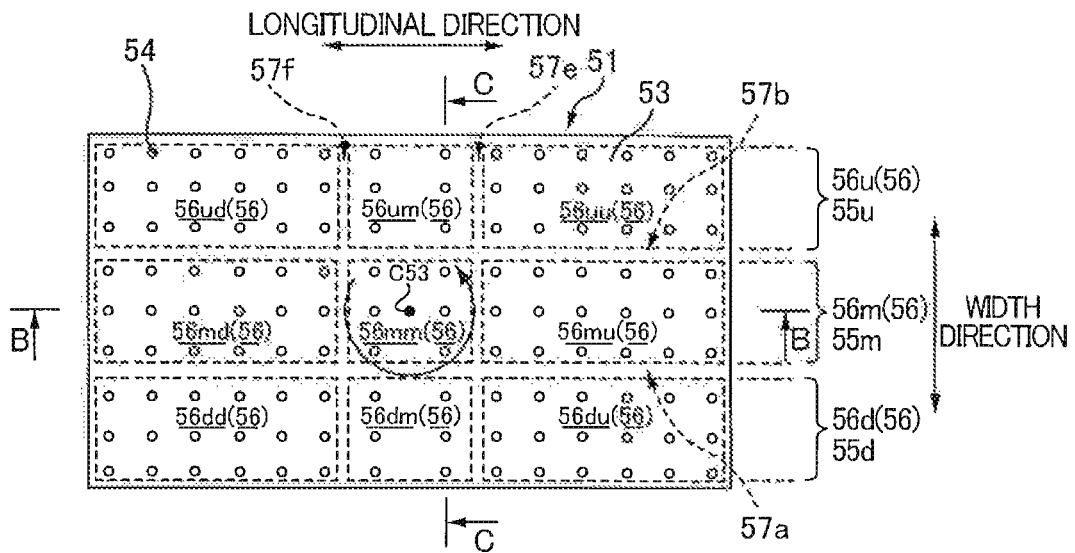
FIG. 16A is a plan view showing a division of a suction chamber 56 in the workpiece holding pallet 51 according to another embodiment mode.
Figure 16B:
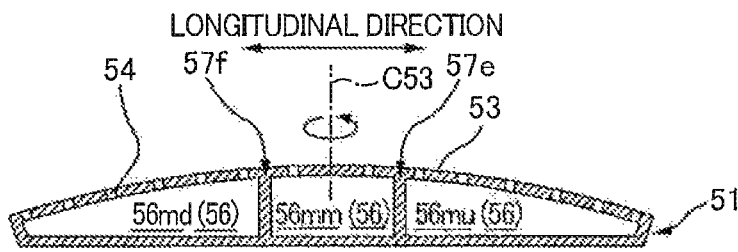
FIG. 16B is a B-B cross section view in FIG. 16A.
Figure 16C:
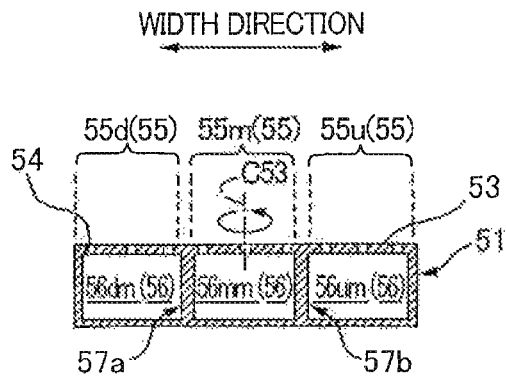
FIG. 16C is a C-C cross section view in FIG. 16A.

For example, in the example in FIG. 16A to FIG. 16C, two division walls 57*e*, 57*f* along the width direction are arranged side by side in the longitudinal direction, and with these division walls 57*e*, 57*f* the suction chamber 56*d* is partitioned into three suction chambers 56*dd*, 56*dm*, 56*du* that do not allow air to pass through to each other, the suction chamber 56*m* is partitioned into three suction chambers 56*md*, 56*mm*, 56*mu* that do not allow air to pass through to each other, and the suction chamber 56*u* is partitioned into three suction chambers 56*ud*, 56*um*, 56*uu* that do not allow air to pass through to each other.

Then, in the case with the above partitions, if further configured as below, holding property can be increased not only during delivery bur also during receiving of the absorbent main body 10, and it will be more preferable.

First, the configuration of the middle chamber member 83 is similar to the above-described embodiment mode. In other words, as shown in FIG. 12B, the internal space of the middle chamber member 83 is partitioned into three chambers 84 in a direction along the trajectory Tr. More specifically, from the downstream side to the upstream side of the trajectory Tr, the internal space is partitioned into the downstream side chamber 84*d*, the middle chamber 84*m*, and the upstream side chamber 84*u*. Further, the middle chamber member 83 is fixed immovably to the rotating drum 42, and the relative positional relationship of these chambers 84*d*, 84*m*, 84*u* to each other is non-changing.

On the contrary, the workpiece holding pallet 51 turns about the turning center of axis C53, so that the positional relationship between the suction chambers 56, 56, . . . 56 in the upstream and downstream direction of the trajectory Tr changes, between a state in which the longitudinal direction of the workpiece holding pallet 51 is facing the CD direction and a state in which it is facing the MD direction.

Then, in respect to this point, it is preferable that regardless of whether the workpiece holding pallet 51 is facing the MD direction or the CO direction, the suction chamber 56 that is relatively positioned in the downstream side in its direction may be configured to be in communication with the downstream side chamber 84*d* of the middle chamber member 83 so as to allow air to pass through, the suction chamber 56 that is relatively positioned in the center may be configured to be in communication with the middle chamber 84*m* of the middle chamber member 83 so as to allow air to pass through, and the suction chamber 56 that is relatively positioned in the upstream side may be configured to be in communication with the upstream side chamber 84*u* of the middle chamber member 83 so as to allow air to pass through.

Figure 17A:
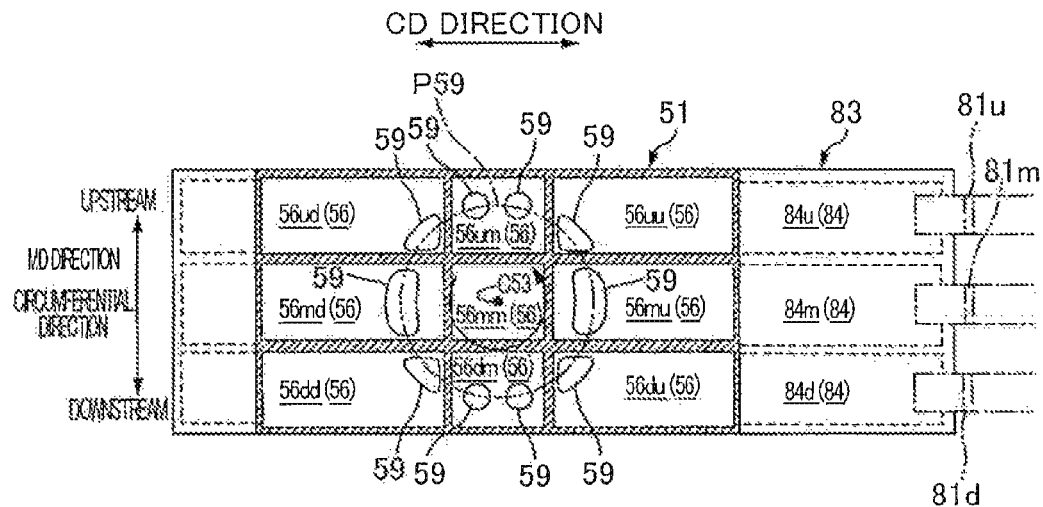
FIG. 17A is an illustrative picture of a state in which a longitudinal direction of the workpiece holding pallet 51 is facing toward a CD direction.

That is to say, as shown in FIG. 17A, in a state in which the longitudinal direction of the workpiece holding pallet 51 is facing the CD direction, the downstream side chamber 84*d* is in communication with the suction chambers 56*dd*, 56*dm*, 56*du* relatively positioned in the downstream side in this state, the middle chamber 84*m* is in communication with the suction chambers 56*md*, 56*mm*, 56*mu* relatively positioned in the center, and the upstream side chamber 84*u* is in communication with the suction chambers 56*ud*, 56*um*, 56*uu* relatively positioned in the upstream side. But on the other hand, as shown in FIG. 17B, in a state in which the longitudinal direction of the workpiece holding pallet 51 is facing the MD direction, the downstream side chamber 84*d* may be configured to be in communication with the suction chambers 56*dd*, 56*md*, 56*ud* relatively positioned in the downstream side in this state, the middle chamber 84*m* may be configured to be in communication with the suction chambers 56*dm*, 56*mm*, 56*um* relatively positioned in the center, and the upstream side chamber 84*u* may be configured to be in communication with the suction chambers 56*du*, 56*mu*, 56*uu* relatively positioned in the upstream side.

Then, with the above configuration, first in the delivery position Qout in FIG. 5, as shown in FIG. 17A, three parties which are the suction chambers 56*dd*, 56*dm*, 56*du* relatively positioned in the downstream side, the suction chambers 56*md*, 56*mm*, 56*mu* relatively positioned in the center, and the suction chambers 56*ud*, 56*um*, 56*uu* relatively positioned in the upstream side may perform the suction operation independently from each other. As a result, as similar to the above-described embodiment mode, decrease in the suction force of the upstream side area 55*u* in the holding surface 53 that may occur in the latter half of the delivery operation can be effectively prevented.

Figure 17B:
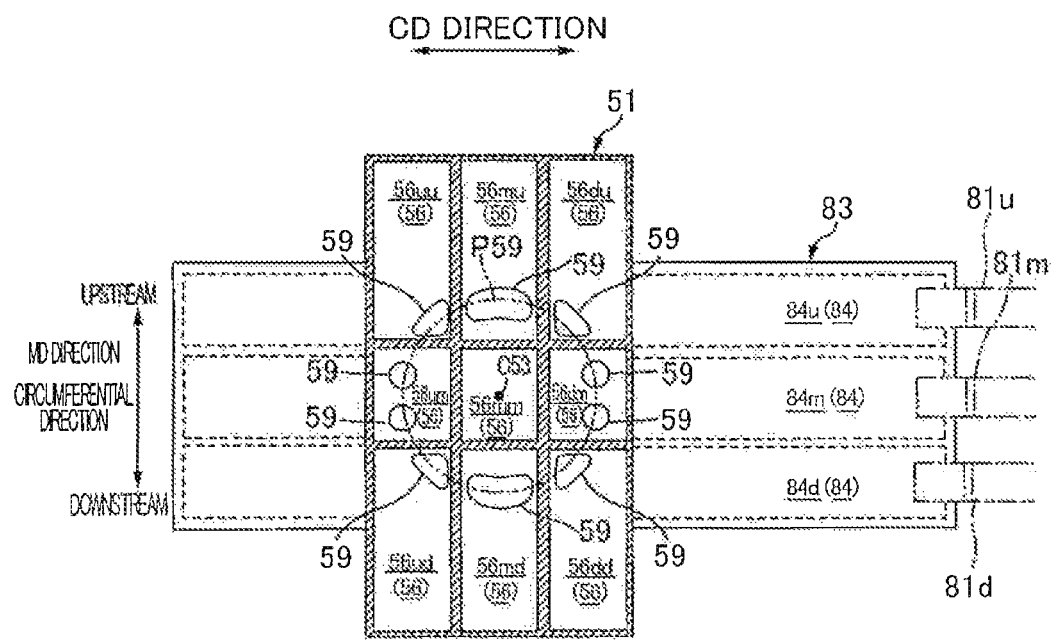
FIG. 17B is an illustrative picture of a state in which this longitudinal direction is facing an MD direction, and both diagrams show the workpiece holding pallet 51 with a part cutaway.

On the other hand, in the receiving position Qin in FIG. 5, as shown in FIG. 17B, three parties of the suction chambers 56*dd*, 56*md*, 56*ud* relatively positioned in the downstream side, the suction chambers 56*dm*, 56*mm*, 56*um* relatively positioned in the center, and the suction chambers 56*du*, 56*mu*, 56*uu* relatively positioned in the upstream side can perform the suction operation independently from each other, so that decrease in the suction force of the holding surface 53 that may occur in the first half of the receiving operation of the absorbent main body 10 as in FIG. 5 can be effectively prevented.

In detail, during the workpiece holding pallet 51 receiving the absorbent main body 10 from the cutter device 61, an area of the holding surface 53 to be covered by the absorbent main body 10 sequentially expands from the downstream side to the upstream side of the trajectory Tr, and finally substantially the entire surface of the holding surface 53 is covered by the absorbent main body 10 and the receiving operation is completed. For this reason, in the first half of the receiving operation, as shown in FIG. 5, only an area in the downstream side of the holding surface 53 is covered by the absorbent main body 10 and an area in the upstream side is in an uncovered state. Here, in the case that only one suction chamber 156 is formed inside the workpiece holding pallet 51 as in the suction configuration of the general example described above in FIG. 9, also in the receiving position Qin, a problem of decrease in the suction force similar to that described above in the delivery position Qout may occur. That is to say, in the first half of the receiving operation, as shown in FIG. 5, an area in the upstream side with a small suction resistance and that is not covered by the absorbent main body 10 leads in sucking the outside air into the suction chamber 156, and as a result the negative pressure level of the suction chamber 156 is extremely decreased, and holding property of the absorbent main body 10 in the area in the downstream side is significantly decreased.

In regards to this point, as shown in FIG. 17B described above, in the case the suction chambers 56d, 56m, 56u are further partitioned into three in the longitudinal direction of the holding surface 53, the suction chambers 56dd, 56md, 56ud corresponding to the area in the downstream side and the suction chambers 56du, 56mu, 56uu corresponding to the area in the upstream side can perform the suction operation independently from each other, so that decrease in the suction force in the area in the downstream side that may occur in the first half of the receiving operation of the absorbent main body 10 can be effectively prevented. As a result, poor holding of the absorbent main body 10 can also be effectively prevented.

As a specific example with such a configuration, the below configuration can be illustrated. First, as shown in FIG. 17A, in a state the turning center of axis C53 of the workpiece holding pallet 51 is aligned to a central position in the upstream and downstream direction (width direction) of the middle chamber member 83, the workpiece holding pallet 51 is arranged superposed on the middle chamber member 83. Further, in a region of a wail section of the workpiece holding pallet 51 opposing the middle chamber member 83, and a region above a perfect circle pitch circle P59 with a center as the turning center of axis C53, at least one or more through hole 59 is formed for each suction chamber 56, 56, ... 56 excluding the middle suction chamber 56mm (the suction chamber 56mm positioned with the turning center of axis C53). Further, when the workpiece holding pallet 51 is facing the CD direction and the MD direction as shown FIG. 17A and FIG. 17B, the through hole 89 is formed also in a region opposing the through hole 59 of the workpiece holding pallet 51 in a wail section of the middle chamber member 83 (refer to FIG. 18).

Figure 18:
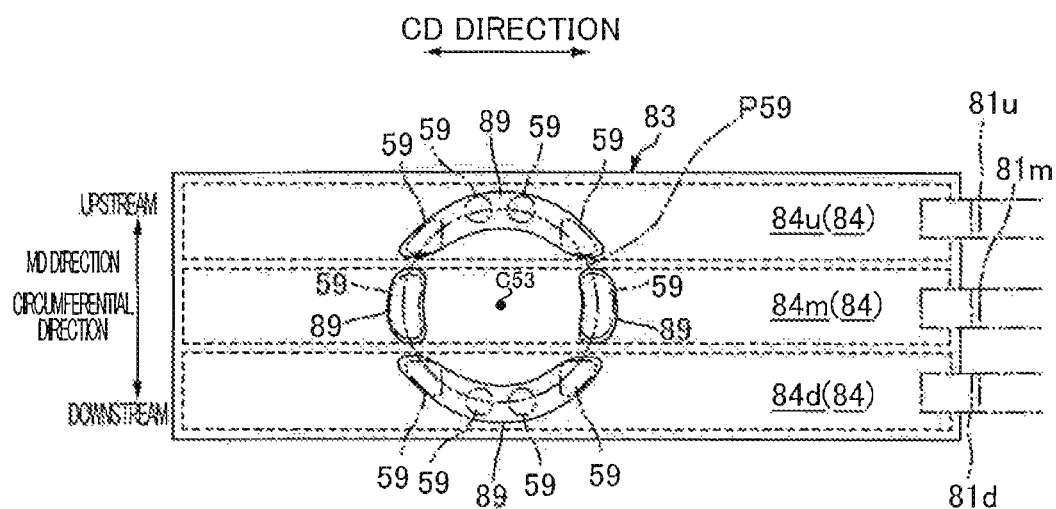
FIG. 18 is an illustrative picture of a middle chamber member 83 shown with the workpiece holding pallet 51 taken off.

Then, here, as shown in FIG. 18, these through holes 89 are not formed across the chambers 84d, 84m, 84u, and any of the through holes 89 are formed in a size in which it can fit in the chamber 84 that the through hole 89 belongs to. Further, as shown in FIG. 17A or FIG. 17B, the through hole 59 of each suction chamber 56 is not formed across adjacent suction chambers 56, 56, and any of the through holes 59 are formed in a size in which it can fit in the suction chamber 56 that the through hole 59 belongs to.

Therefore, as shown in FIG. 17A and FIG. 17B, regardless of whether the workpiece holding pallet 51 is facing the CD direction or the MD direction, the suction chambers 56, 56, 56 relatively positioned in the downstream side in its direction are in communication with only the downstream side chamber 84d, the suction chambers 56, 56 relatively positioned in the center are in communication with only the middle chamber 84m, and the suction chambers 56, 56, 56 relatively positioned in the upstream side are in communication with only the upstream side chamber 84u. As a result, the suction chambers 56, 56, 56 relatively positioned in the downstream side, the suction chambers 56, 56 relatively positioned in the center, and the suction chambers 56, 56, 56 relatively positioned in the upstream side can perform the suction operation independently in a state partitioned so as not to allow air to pass through to each other.

REFERENCE SIGNS LIST 1 disposable diaper (absorbent article),
1a semifinished product (composite body of sheet-like member of absorbent article),
3 torso opening, 5 leg opening,
10 absorbent main body (first sheet-like member),
10a continuous body of absorbent main body, 10e end section,
11 absorbent body, 12 surface sheet member,
13 back surface sheet member, 14 leakproof sheet,
15 exterior sheet, 16 fluid permeable sheet, 17 elastic member,
20 abdominal side belt member,
20a continuous body of belt member (second sheet-like member),
21 nonwoven fabric, 24 back side belt member,
24a continuous body of belt member (second sheet-like member),
31 manufacturing equipment,
41 rotating drum device, 42 rotating drum,
51 workpiece holding pallet (holding section), 53 holding surface, 54 suction hole (hole), 55 suction area,
55d downstream side suction area, 55m middle suction area, 55u upstream side suction area,
56 suction chamber,
56d downstream side suction chamber (first suction chamber),
56m middle suction chamber,
56u upstream side suction chamber (second suction chamber),
56dd suction chamber, 56dm suction chamber, 56du suction chamber,
56md suction chamber, 56mm suction chamber, 56mu suction chamber,
56ud suction chamber, 56um suction chamber, 56uu suction chamber,
57a division wall, 57b division wall,
57c division wall, 57d division wall,
57e division wall, 57f division wall,
59 through hole,
59d recessed section, 59m recessed section, 59u recessed section,
61 cutter device, 61a upper roll, 61b lower roll, 62 flat blade,
71 transport roller, 81 suction pipe,
81d downstream side suction pipe, 81m middle suction pipe,
81u upstream side suction pipe,
82a one end opening, 82b other end opening,
83 middle chamber member, 84 chamber,
84d downstream side chamber, 84m middle chamber,
84u upstream side chamber,
85 negative pressure chamber drum,
89 through hole, 92 movable wall, 156 suction chamber,
BL boundary line, BLd boundary line,
BLm boundary line, BLu boundary line,
Tr trajectory,
Z0 non-negative pressure zone, Z1 negative pressure zone,
C10 central section,
C41 center of axis, C53 center of turning axis,
C61a center of axis, C61b center of axis, C71 center of axis,
P59 pitch circle,
Qin receiving position, Qout delivery position

The invention claimed is:
1. A method of manufacturing a composite body of a sheet-shaped member of an absorbent article, the method comprising:
receiving a first sheet-shaped member on a holding surface of a holding section at a receiving position;
holding the first sheet-shaped member on the holding surface of the holding section; and delivering and attaching the first sheet-shaped member from the holding surface to a second sheet-shaped member at a transport roller located at a delivery position, wherein the first sheet-shaped member has a section that is to be delivered first and a section that is to be delivered subsequently during delivery to the second sheet-shaped member, the first sheet-shaped member is held on the holding surface with suction force from a plurality of holes formed on the holding surface, the holding section having at least first and second suction chambers, wherein the first suction chamber is in communication with holes that suck the section that is to be delivered first, and the second suction chamber is in communication with holes that suck the section that is to be delivered subsequently, the first sheet-shaped member is delivered to the second sheet-shaped member in a state in which the first suction chamber and the second suction chamber have been partitioned so as not to allow air to pass through to each other, at the delivery position, suction operation of the first suction chamber is performed by a first suction pipe, and suction operation of the second suction chamber is performed by a second suction pipe, and at the receiving position, the first suction chamber is in communication with the first suction pipe and the second suction pipe, and suction operation of the first suction chamber is performed by cooperation of the first suction pipe and the second suction pipe which are in communication with the first suction chamber, and the second suction chamber is in communication with the first suction pipe and the second suction pipe, and suction operation of the second suction chamber is performed by cooperation of the first suction pipe and the second suction pipe which are in communication with the second suction chamber, wherein the holding section is supported by a rotating drum and turnable about a turning axis of the holding section, the turning axis of the holding section passes through a center of the holding surface along a radius direction of the rotating drum, the holding surface has end sections and a central section between the end sections in a longitudinal direction of the holding surface, the holding surface has a convex shape where the central section bulges outward in the radius direction more than the end sections, wherein the transport roller has a central section having a concave external shape in correspondence with the convex shape of the holding surface, wherein a negative pressure chamber drum has a cylindrical body arranged co-axially with the rotating drum and rotates at a same speed as the rotating drum, the cylindrical body has a doughnut-shaped internal space divided, in a circumferential direction of the negative pressure chamber drum and by a partition wall, into a negative pressure zone as a negative pressure source, and a non-negative pressure zone, the negative pressure zone is set corresponding to an angular range from the receiving position to the delivery position, the non-negative pressure zone is set corresponding to another angular range from the delivery position to the receiving position, and wherein a middle chamber member arranged between the negative pressure chamber drum and the holding section in the radius direction is in communication with the internal space of the negative pressure chamber drum via the first suction pipe and the second suction pipe.

2. The manufacturing method as claimed in claim 1, wherein in response to a delivery operation of the section to be delivered first to the second sheet-shaped member, suction force of the holes that suck the section to be delivered first is weakened, and in response to a delivery operation of the section to be delivered subsequently to the second sheet-shaped member, suction force of the holes that suck the section to be delivered subsequently is weakened.

3. The manufacturing method as claimed in claim 2, wherein the holes where suction force has been weakened blow out air toward the first sheet-shaped member in an order in which suction force of the holes has been weakened.

4. The manufacturing method as claimed in claim 1, wherein a third suction chamber is partitioned in a position in between the first suction chamber and the second suction chamber in the holding section, holes in communication with the third suction chamber are positioned in between the holes in communication with the first suction chamber and the holes in communication with the second suction chamber, and in a state in which the first suction chamber, the second suction chamber, and the third suction chamber have been partitioned so as not to allow air to pass through to each other, the first sheet-shaped member is delivered to the second sheet-shaped member.

5. The manufacturing method as claimed in claim 1, wherein the holding section moves along a trajectory, the second sheet-shaped member is a continuous sheet that is wrapped around the transport roller at the delivery position in the trajectory and that travels continuously in a travel direction, during the holding section passing by the delivery position along the travel direction of the second sheet-shaped member, the first sheet-shaped member on the holding surface of the holding section is delivered to the second sheet shaped member, and the holes that suck the section to be delivered first are formed in an area to be a downstream side in the trajectory of the holding surface during delivery, and the holes that suck the section to be delivered subsequently are formed in an area to be an upstream side in the trajectory of the holding surface.

6. The manufacturing method as claimed in claim 1, wherein the section to be delivered first and the section to be delivered subsequently are each fixed with an elastic member that contracts these sections toward each other, and in a state in which the first sheet-shaped member is sucked onto the holding surface with the suction force from the holes, the section to be delivered first and section to be delivered subsequently are held in a state extended against a contractive force from the corresponding elastic member.

7. The manufacturing method as claimed in claim 1, wherein
the first suction chamber and the second suction chamber are chambers partitioned inside the holding section so as not to allow air to pass through to each other.

8. A manufacturing equipment for manufacturing a composite body of a sheet-shaped member of an absorbent article, said equipment comprising:
a rotating drum having a radius direction;
a holding section supported by the rotating drum and including a holding surface;
a negative pressure chamber drum having a cylindrical body arranged co-axially with the rotating drum, the negative pressure chamber drum being configured to rotate at a same speed as the rotating drum;
a middle chamber member arranged between the negative pressure chamber drum and the holding section in the radius direction; and
a transport roller;
the holding section configured to
receive a first sheet-shaped member on the holding surface of the holding section at a receiving position,
hold the first sheet-shaped member on the holding surface, and
deliver and attach the first sheet-shaped member to the second sheet-shaped member at the transport roller located at a delivery position,
wherein
the holding surface includes a plurality of holes,
the first sheet-shaped member has a section to be delivered first and a section to be delivered subsequently during delivery to the second sheet-shaped member,
the holding section is configured to hold the first sheet-shaped member on the holding surface with suction force from the plurality of holes formed on the holding surface,
the holding section has at least first and second suction chambers, the first suction chamber is in communication with holes for sucking the section to be delivered first and the second suction chamber is in communication with holes for sucking the section to be delivered subsequently,
the holding section is further configured to deliver the first sheet-shaped member to the second sheet-shaped member in a state in which the first suction chamber and the second suction chamber have been partitioned so as not to allow air to pass through to each other,
the holding section is turnable about a turning axis thereof, the turning axis of the holding section passing through a center of the holding surface along the radius direction of the rotating drum
at the delivery position,
the first suction chamber is configured to perform suction operation by a first suction pipe, and
the second suction chamber is configured to perform suction operation by a second suction pipe, and
at the receiving position,
the first suction chamber is in communication with the first suction pipe and the second suction pipe, and configured to perform suction operation by cooperation of the first suction pipe and the second suction pipe which are in communication with the first suction chamber, and
the second suction chamber is in communication with the first suction pipe and the second suction pipe, and configured to perform suction operation by cooperation of the first suction pipe and the second suction pipe which are in communication with the second suction chamber,
wherein
the holding section has end sections and a central section between the end sections in longitudinal direction of the holding surface,
the holding surface has a convex shape where the central section bulges outward in the radius direction more than the end sections,
wherein
the transport roller has a central section having a concave external shape in correspondence with the convex shape of the holding surface,
wherein
the cylindrical body of the negative pressure chamber drum has a doughnut-shaped internal space divided, in a circumferential direction of the negative pressure chamber drum and by a partition wall, into
a negative pressure zone as a negative pressure source, and
a non-negative pressure zone,
the negative pressure zone is set corresponding to an angular range from the receiving position to the delivery position, and
the non-negative pressure zone is set corresponding to another angular range from the delivery position to the receiving position, and
wherein
the middle chamber member is in communication with the internal space of the negative pressure chamber drum via the first suction pipe and the second suction pipe.

9. The manufacturing equipment according to claim 8, wherein
in response to a delivery operation of the section to be delivered first to the second sheet-shaped member, suction force of the holes for sucking the section to be delivered first is configured to be weakened, and
in response to a delivery operation of the section to be delivered subsequently to the second sheet-shaped member, suction force of the holes for sucking the section to be delivered subsequently is configured to be weakened.

10. The manufacturing equipment according to claim 9, wherein the holes of which the suction force has been weakened are configured to blow out air toward the first sheet-shaped member in an order in which the suction force of the holes has been weakened.

11. The manufacturing equipment according to claim 8, wherein
the holding section further comprises a third suction chamber partitioned in a position in between the first suction chamber and the second suction chamber,
holes in communication with the third suction chamber are positioned in between the holes in communication with the first suction chamber and the holes in communication with the second suction chamber, and
the holding section is configured to deliver the first sheet-shaped member to the second sheet-shaped member in a state in which the first suction chamber, the second suction chamber, and the third suction chamber have been partitioned so as not to allow air to pass through to each other.

12. The manufacturing equipment according to claim 8, wherein
- the holding section is configured to move along a trajectory,
- the transport roller is configured to move the second sheet-shaped member continuously in a travel direction, the second sheet-shaped member is a continuous sheet and is configured to be wrapped around the transport roller at the delivery position in the trajectory,
- the holding section is configured to deliver the first sheet-shaped member on the holding surface to the second sheet-shaped member during the holding section passes by the delivery position along the travel direction of the second sheet-shaped member, and
- the holes for sucking the section to be delivered first are located in an area on a downstream side in the trajectory of the holding surface, and the holes for sucking the section to be delivered subsequently are located in an area on an upstream side in the trajectory of the holding surface.

13. The manufacturing equipment according to claim 8, wherein
in a state in which the first sheet-shaped member is sucked onto the holding surface with the suction force from the holes, the holding section is configured to hold the section to be delivered first and the section to be delivered subsequently, which are each fixed with an elastic member that contracts the section to be delivered first and the section to be delivered subsequently toward each other, in a state extended against a contractive force from the corresponding elastic member.

14. The manufacturing equipment according to claim 8, wherein the first suction chamber and the second suction chamber are chambers partitioned inside the holding section so as not to allow air to pass through to each other.

15. The manufacturing equipment according to claim 8, wherein the holding section is configured to turn 90 degrees about the turning axis between the delivery position and the receiving position.

16. The manufacturing method according to claim 1, wherein the holding section turns 90 degrees about the turning axis between the delivery position and the receiving position.

* * * * *